US012059369B2

United States Patent
Kochem et al.

(10) Patent No.: US 12,059,369 B2
(45) Date of Patent: Aug. 13, 2024

(54) VARIABLE STIFFNESS FLEXURE

(71) Applicant: HOLOGIC, INC., Marlborough, MA (US)

(72) Inventors: Thomas C. Kochem, Watertown, MA (US); Daniel A. Beaudet, Lexington, MA (US); Stephen Perry, Shirley, MA (US)

(73) Assignee: Hologic, Inc., Marlborough, MA (US)

( * ) Notice: Subject to any disclaimer, the term of this patent is extended or adjusted under 35 U.S.C. 154(b) by 862 days.

(21) Appl. No.: 16/825,964

(22) Filed: Mar. 20, 2020

(65) Prior Publication Data

US 2020/0214879 A1    Jul. 9, 2020

Related U.S. Application Data

(63) Continuation of application No. 15/636,514, filed on Jun. 28, 2017, now Pat. No. 10,624,780, which is a continuation of application No. 14/805,953, filed on Jul. 22, 2015, now Pat. No. 9,693,890, which is a continuation of application No. 13/447,728, filed on Apr. 16, 2012, now abandoned.

(51) Int. Cl.
  *A61F 6/14*        (2006.01)
  *A61F 6/18*        (2006.01)
(52) U.S. Cl.
  CPC .............. *A61F 6/144* (2013.01); *A61F 6/142* (2013.01); *A61F 6/18* (2013.01)
(58) Field of Classification Search
  CPC .. A61F 6/144; A61F 6/142; A61F 6/18; A61F 6/14; A61B 18/1485; A61B 2018/00577; A61B 2018/00559; A61B 17/4241; A61B 2017/4216; A61B 5/4325; A61B 5/6875; A61B 10/0291; A61B 18/12; A61B 18/14; A61B 2018/00214

USPC ................................................. 128/833, 840
See application file for complete search history.

(56) References Cited

U.S. PATENT DOCUMENTS

| | | | | |
|---|---|---|---|---|
| 2005/0085880 A1* | 4/2005 | Truckai | ............. | A61M 16/0427 607/101 |
| 2012/0179155 A1* | 7/2012 | Strul | ................... | A61B 18/1206 606/33 |
| 2012/0283724 A1* | 11/2012 | Toth | ................... | A61B 18/1485 606/41 |

FOREIGN PATENT DOCUMENTS

CN            2150840 Y  *  2/1993   ............. A61F 6/144

OTHER PUBLICATIONS

Translation of CN-2150840-Y (Year: 1993).*

* cited by examiner

*Primary Examiner* — Keri J Nelson
*Assistant Examiner* — Seth R. Brown
(74) *Attorney, Agent, or Firm* — Vista IP Law Group, LLP

(57) ABSTRACT

An intrauterine device includes a central support member, first and second internal flexures and first and second external flexures. The first and second internal flexures each include a first section having a first stiffness, a second section having a second stiffness, and third section having a third stiffness, wherein the second stiffness is more flexible than the first and third stiffness and wherein the first section of each internal flexure is coupled to the central support member. The first and second external flexures are coupled to the central support member and coupled to the third sections of the first and second internal flexures, the first and second external flexures in combination with the first and second internal flexures being configured to extend from a (Continued)

collapsed position parallel to the central support member to a deployed position flexing away from the central support member.

18 Claims, 15 Drawing Sheets

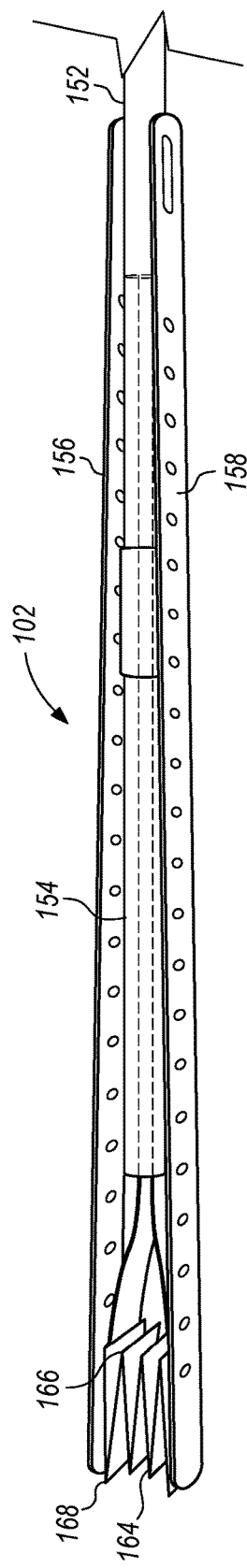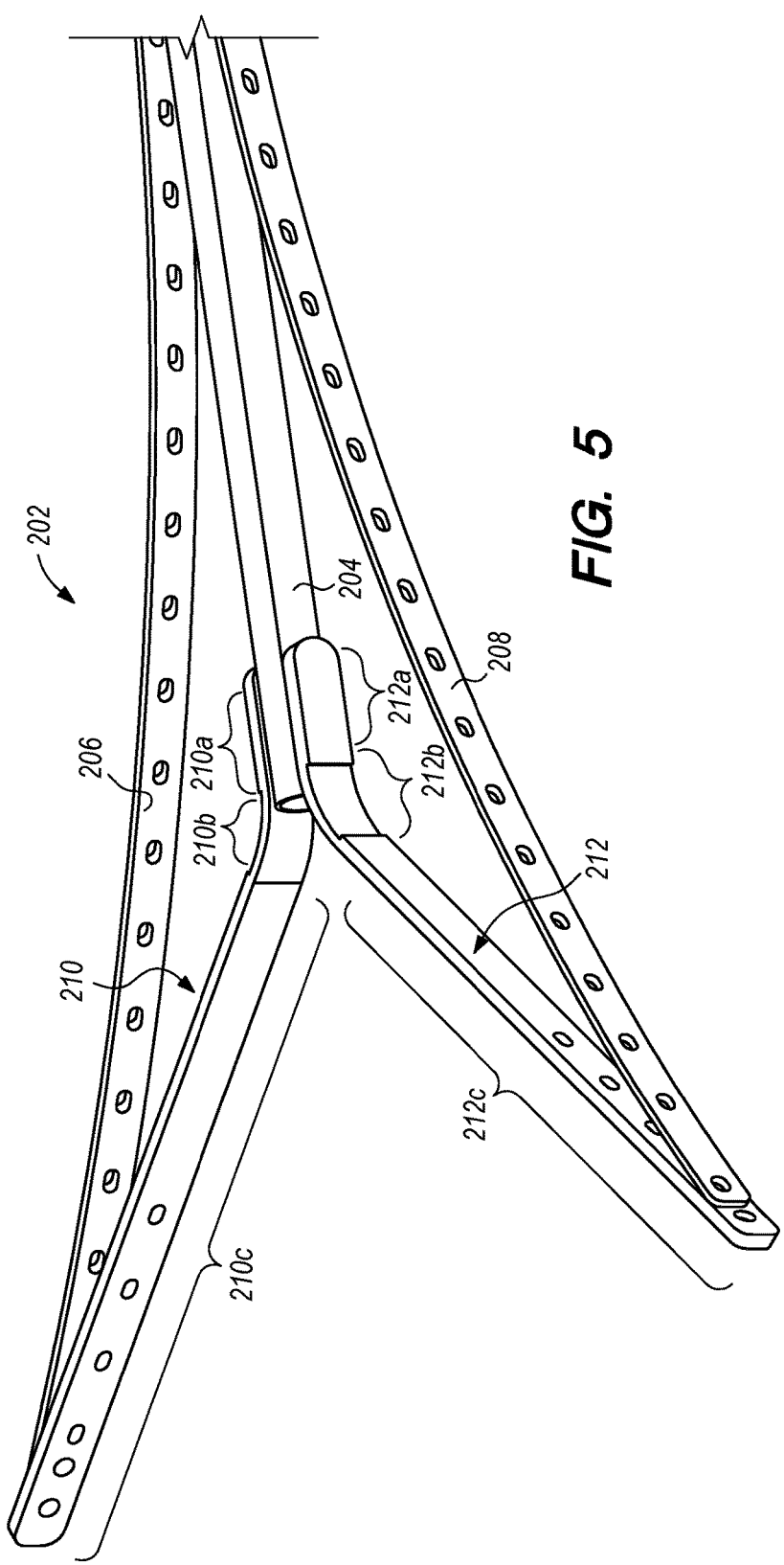

VARIABLE STIFFNESS FLEXURE

RELATED APPLICATION DATA

This application is a continuation of pending U.S. patent application Ser. No. 15/636,514, filed Jun. 28, 2017, which is a continuation of U.S. Pat. No. 9,693,890, filed Jul. 22, 2015, which is a continuation of U.S. patent application Ser. No. 13/447,728, filed Apr. 16, 2012, now abandoned, the priority of which is claimed under 35 U.S.C. § 120.

BACKGROUND

Intrauterine medical devices are often inserted through a patient's cervix and then expanded inside the patient's uterus. For example, a uterine ablation procedure may be performed by inserting a sheath through the cervix and then extending an applicator through the distal end of the sheath and expanding the applicator in the uterus. The applicator is expanded inside the patient, out of view of the person performing the procedure. Reliable and proper deployment of the applicator and subsequent robustness of the device are important to avoid complications and potential injury to the patient. Additionally, the applicator should reliably contract back into the sheath for removal from the patient.

SUMMARY

Aspects and embodiment are directed to reducing the diameter of the sheath of an intrauterine device while maintaining the strength and robustness of the device. Reducing the diameter of the sheath of an intrauterine device improves its ease of insertion and decreases patient discomfort.

According to one aspect, a device includes a central support member, first and second internal flexures, and first and second external flexures. The device may be an intrauterine device. The first and second internal flexures each include a first section having a first stiffness, a second section having a second stiffness, and third section having a third stiffness, wherein the second stiffness is more flexible than the first and third stiffness and wherein the first section of each internal flexure is coupled to the central support member. The first and second external flexures are each coupled to the central support member and are each coupled to the third section of the respective first and second internal flexures. The first and second external flexures, in combination with the first and second internal flexures, are configured to extend from a collapsed position parallel to the central support member to a deployed position flexing away from the central support member. In one embodiment, the device is an endometrial ablation device. According to one feature, stiffness refers to the bending characteristics of the flexure.

According to one embodiment, the first and second internal flexures further include a fourth section having a fourth stiffness and a fifth section having a fifth stiffness. The fourth section is positioned between the first section and the second section and the fifth section is positioned between the second section and the third section. The fourth and fifth stiffnesses are more flexible than the first and third stiffnesses and less flexible than the second stiffness. In one embodiment, the fourth and fifth stiffnesses taper, decreasing in stiffness toward the second section.

In another embodiment, the device also includes a bridge coupled between the first and second external flexures. The bridge may be configured to fold in the first position and to at least partially extend in the second position. In one embodiment, the device includes a mesh array surrounding the first and second external flexures, the first and second internal flexures and the central support member.

According to another aspect, a device includes a central support member, first and second internal flexures, and first and second external flexures. In one embodiment, the device is an intrauterine device. The first and second internal flexures each include a first section having a first stiffness and a second section having a second stiffness, wherein the second stiffness is less than the first stiffness and wherein the first section of each internal flexure is coupled to the central support member. The first and second external flexures are each coupled to the central support member and are each coupled to the second section of the respective first and second internal flexures. The first and second external flexures, in combination with the first and second internal flexures, are configured to extend from a collapsed position parallel to the central support member to a deployed position flexing away from the central support member. In one embodiment, the device is an endometrial ablation device.

According to one aspect, a device includes a central support member having a center line, first and second internal flexures each including first and second sections, and first and second external flexures. The first section is positioned adjacent to the second section, and in one example, the first section is stacked on the second section. The first section includes a middle portion, and the middle portion has a C-shape, wherein the middle portion curves inward toward a center line and curves outward toward the second stacked section. The first and second external flexures are each coupled to the central support member and each coupled near a distal end of the respective first and second internal flexures. The first and second external flexures, in combination with the first and second internal flexures, are configured to extend from a collapsed position parallel to the central support member to a deployed position flexing away from the central support member. In one embodiment, the device is an intrauterine endometrial ablation device.

In one embodiment, the intrauterine device also includes a sheath configured to enclose the central support member, the first and second internal flexures and the first and second external flexures when in a collapsed and retracted position. In another embodiment, the device includes a mesh array supported by the first and second external flexures, the first and second internal flexures and the central support member. The mesh array may be comprised of a conductive material.

According to another aspect, a device includes a central support member, first and second sets of internal flexures, and first and second external flexures. The first set of internal flexures includes two internal flexures, and the proximal end of each internal flexure is coupled to the central support member at a first position. The second set of internal flexures includes two internal flexures, and the proximal end of each internal flexure is coupled to the central support member at a second position, wherein the second position is distal to the first position. The first and second external flexures are each coupled to the central support member and are each coupled to distal ends of the first and second sets of internal flexures. The first and second external flexures, in combination with the first and second sets of internal flexures, are configured to extend from a collapsed position parallel to the central support member to a deployed position flexing away from the central support member.

According to one aspect, a device includes a central support member, first and second internal flexures, and first and second external flexures. In one embodiment, the device is an intrauterine device. The first and second internal flexures each include a first section having a first thickness, a second section having a second thickness, and third section having a third thickness, wherein the second thickness is less than the first and third thicknesses and wherein the first section of each internal flexure is coupled to the central support member. The first and second external flexures are each coupled to the central support member and are each coupled to the third section of the respective first and second internal flexures. The first and second external flexures, in combination with the first and second internal flexures, are configured to extend from a collapsed position parallel to the central support member to a deployed position flexing away from the central support member. In one embodiment, the device is an endometrial ablation device.

In one embodiment, the central support member includes two or more support members coupled together. The support members may move relative to one another. The support members may be telescoping support members. In one example, the support members may be slidably coupled together. According to one feature, the first and second internal flexures are attached to a first support member of the central support member, and the first and second external flexures are attached to a second support member of the central support member.

In one embodiment, the first and second internal flexures further include a fourth section having a fourth thickness and a fifth section having a fifth thickness. The fourth section is positioned between the first section and the second section and the fifth section is positioned between the second section and the third section. The fourth and fifth thicknesses are thinner than the first and third thicknesses and thicker than the second thickness. In one embodiment, the fourth and fifth thicknesses taper, decreasing in thickness toward the second section. In another embodiment, the fourth and fifth sections are triangular shaped.

According to one embodiment, the device also includes a bridge coupled between the first and second external flexures. The bridge may be configured to fold in the first position and to at least partially extend in the second position. According to another embodiment, the device also includes a sheath configured to enclose the central support member, the first and second internal flexures and the first and second external flexures when in the first position.

In one embodiment, the device also includes a mesh array surrounding the first and second external flexures, the first and second internal flexures and the central support member. The mesh array may be comprised of a conductive material. In another embodiment, the central support member is a tube.

According to another aspect, a device includes a central support member, first and second internal flexures, and first and second external flexures. In one embodiment, the device is an intrauterine device. The first and second internal flexures each include a first section having a first thickness and a second section having a second thickness, wherein the first thickness is less than the second thickness and wherein the first section of each internal flexure is coupled to the central support member. The first and second external flexures are each coupled to the central support member and are each coupled to the second section of the respective first and second internal flexures. The first and second external flexures, in combination with the first and second internal flexures, are configured to extend from a collapsed position parallel to the central support member to a deployed position flexing away from the central support member. In one embodiment, the device is an endometrial ablation device.

According to another aspect, a method of manufacturing an intrauterine device includes providing a central support member, providing first and second internal flexures to include a first section having a first stiffness, a second section having a second stiffness, and third section having a third stiffness, wherein the second stiffness is more flexible than the first and third stiffness, providing first and second external flexures, attaching the first section of each internal flexure to the central support member, attaching, at a first location, the first and second external flexures to the central support member, and attaching, at a second location, the first and second external flexures to the third section of the respective first and second internal flexures.

According to one embodiment, providing a central support member includes forming a first hollow elongate tubular member, forming a second hollow tubular member, and coupling the first hollow tubular member with the second hollow tubular member. According to another embodiment, providing of the first and second internal flexures includes forming the first and second flexures such that the first section has a first thickness, the second section has a second thickness, and the third section has a third thickness. According to a further embodiment, the forming is done by photoetching.

Still other aspects, embodiments, and advantages of these exemplary aspects and embodiments, are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 4 is a perspective view of an embodiment of a portion of an intrauterine therapy application device applicator in a collapsed position according to aspects of the invention;

FIG. 5 is a perspective view of an embodiment of a portion of an intrauterine therapy application device applicator showing internal flexures according to aspects of the invention;

DETAILED DESCRIPTION

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure.

According to aspects of this disclosure, various structures and methods are provided herein for decreasing a size or diameter of an intrauterine therapy application device in a retracted position, while maintaining its strength and stiffness in expanded and deployed positions. In at least one embodiment, various structures and methods are provided for maintaining the strength of a deployment mechanism of an intrauterine therapy application device by varying the stiffness of at least a portion of the individual flexures of the deployment mechanism.

According aspects of this disclosure, structure and methods are provided to decrease the stiffness of at least a portion of some of the flexures of a deployment mechanism of an intrauterine therapy application device, without increasing the risk of buckling of the deployment mechanism of intrauterine therapy application device. One advantage of decreasing the stiffness of least a portion of some of the flexures of the deployment mechanism of the intrauterine therapy application device is a reduced size or diameter of the intrauterine therapy application device in collapsed position or a retracted into a sheath position, which provides for a smaller-diameter sheath while still maintaining the deployment mechanism's strength and stiffness in collapsed and deployed positions. Another advantage is a smaller outer diameter sheath may reduce patient discomfort and decrease the potential for cervical injury during insertion into the uterus.

Figure 1:
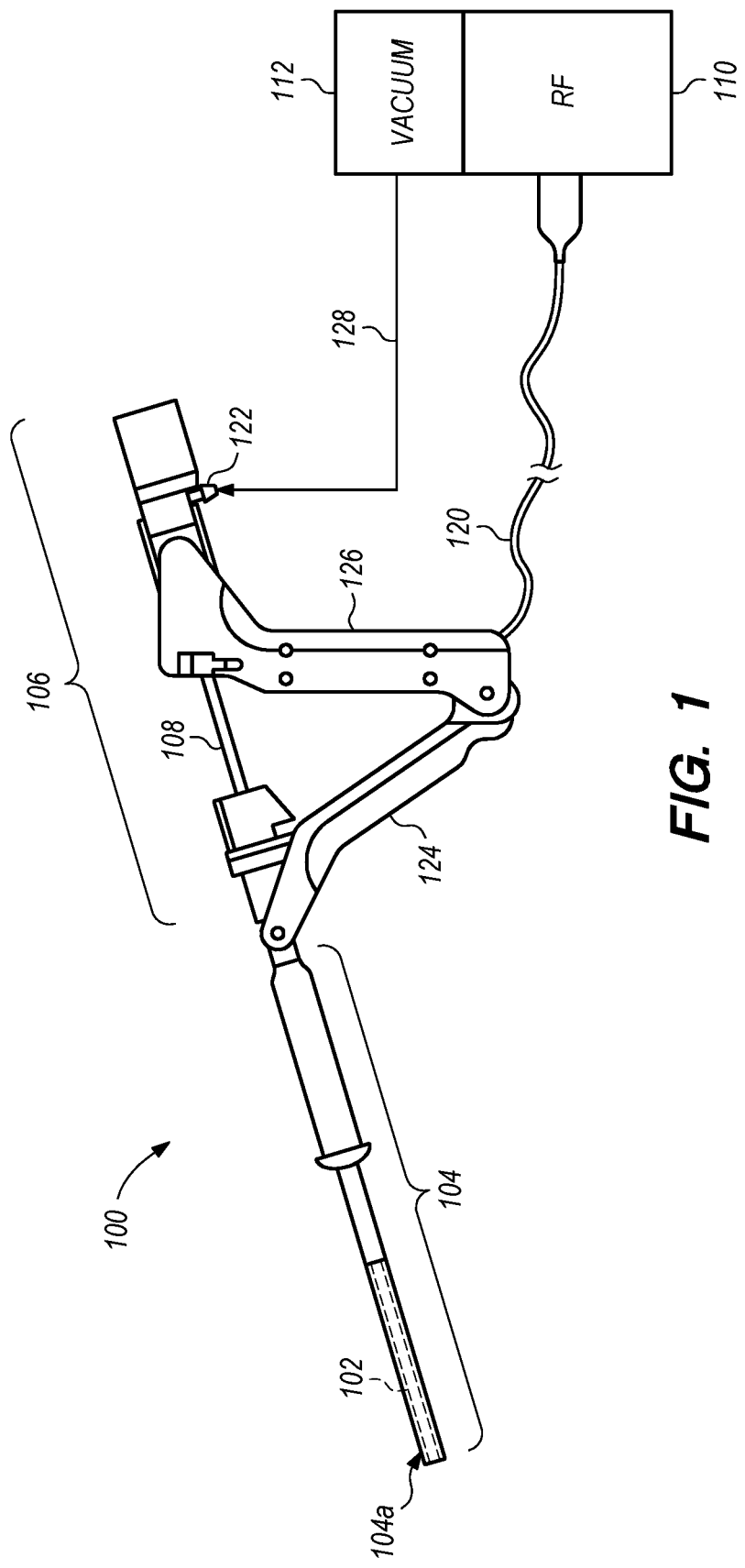
FIG. 1 is a side elevation view of an intrauterine therapy application device with an applicator in a retracted position according to aspects of the invention.

By way of introduction and referring to the Figures, illustrated in FIG. 1 is an intrauterine therapy application device includes an applicator 102, a sheath 104, and an RF generator 110. According to one embodiment, the sheath is inserted through the patient's cervix. The applicator may be retracted in a collapsed position within the sheath for insertion into the patient's cervix. The sheath may be inserted through the patient's cervix, and when the distal end 104a of the sheath is inside the uterus, the applicator may be extended into the uterus in a collapsed position and expanded into a deployed state in the uterus. FIG. 3B illustrates an intrauterine therapy application device applicator 102 in a deployed position and having a mesh array 142. Decreasing the size, such as the width in a collapsed position of the applicator allows for use of a smaller-diameter sheath. A sheath having a smaller outer diameter may reduce patient discomfort, and also decrease the potential for cervical injury during insertion through the cervix and into the uterus. In some embodiments, the deployment mechanism includes internal flexures (see 160, 162 of FIG. 3A) and external flexures (see 156, 158 of FIG. 3A). In a deployed position, external flexures (156, 158 of FIG. 3A) define the outer contour of the applicator, and internal flexures (160, 162 of FIG. 3A) facilitate reliable deployment of the applicator from the sheath into a collapsed position and into a deployed state as well as retraction of the applicator into the collapsed position and into the sheath.

Figure 3A:
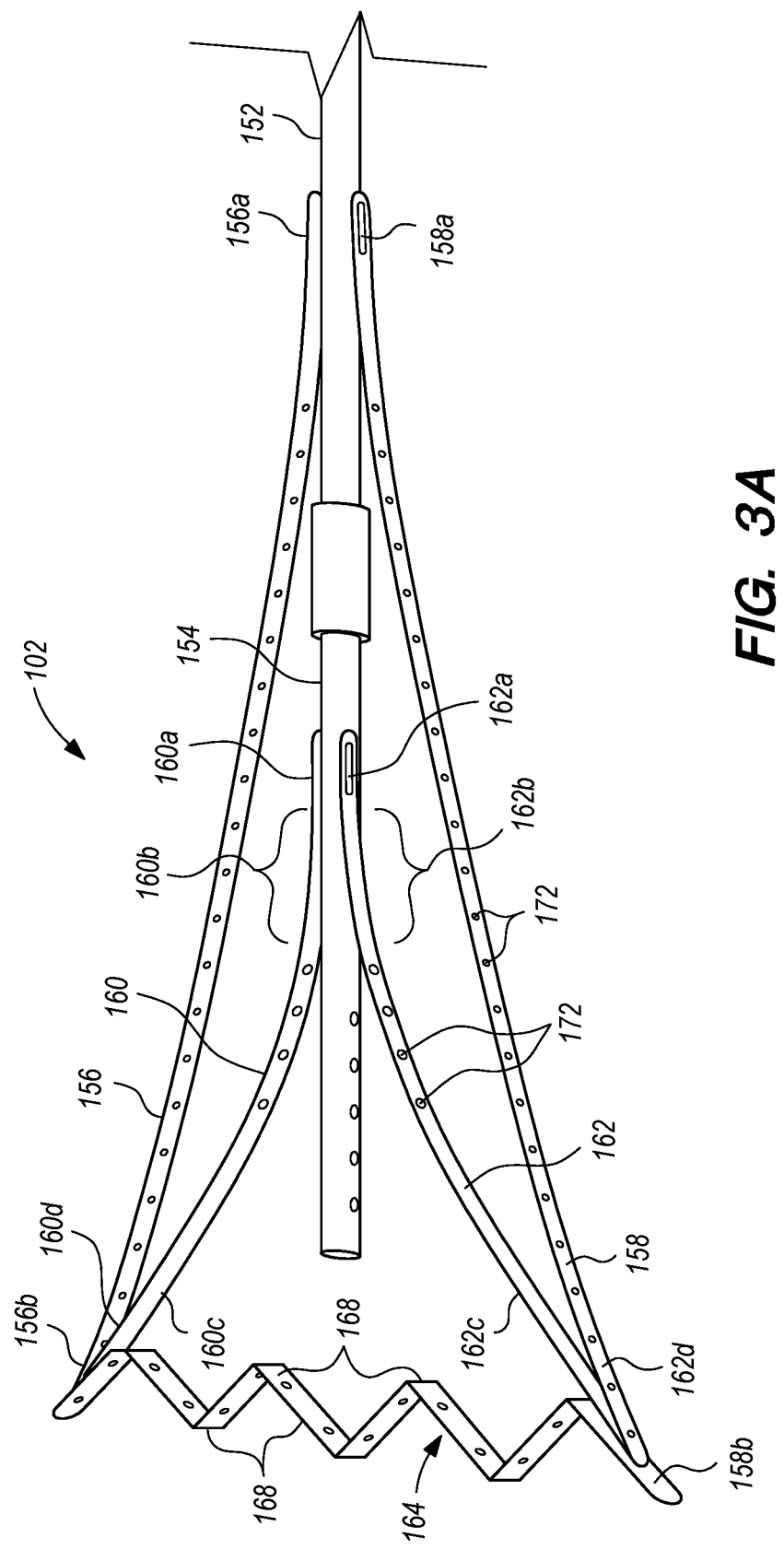
FIG. 3A is a perspective view of an embodiment of an intrauterine therapy application device applicator in a deployed position, according to aspects of the invention.
Figure 3B:
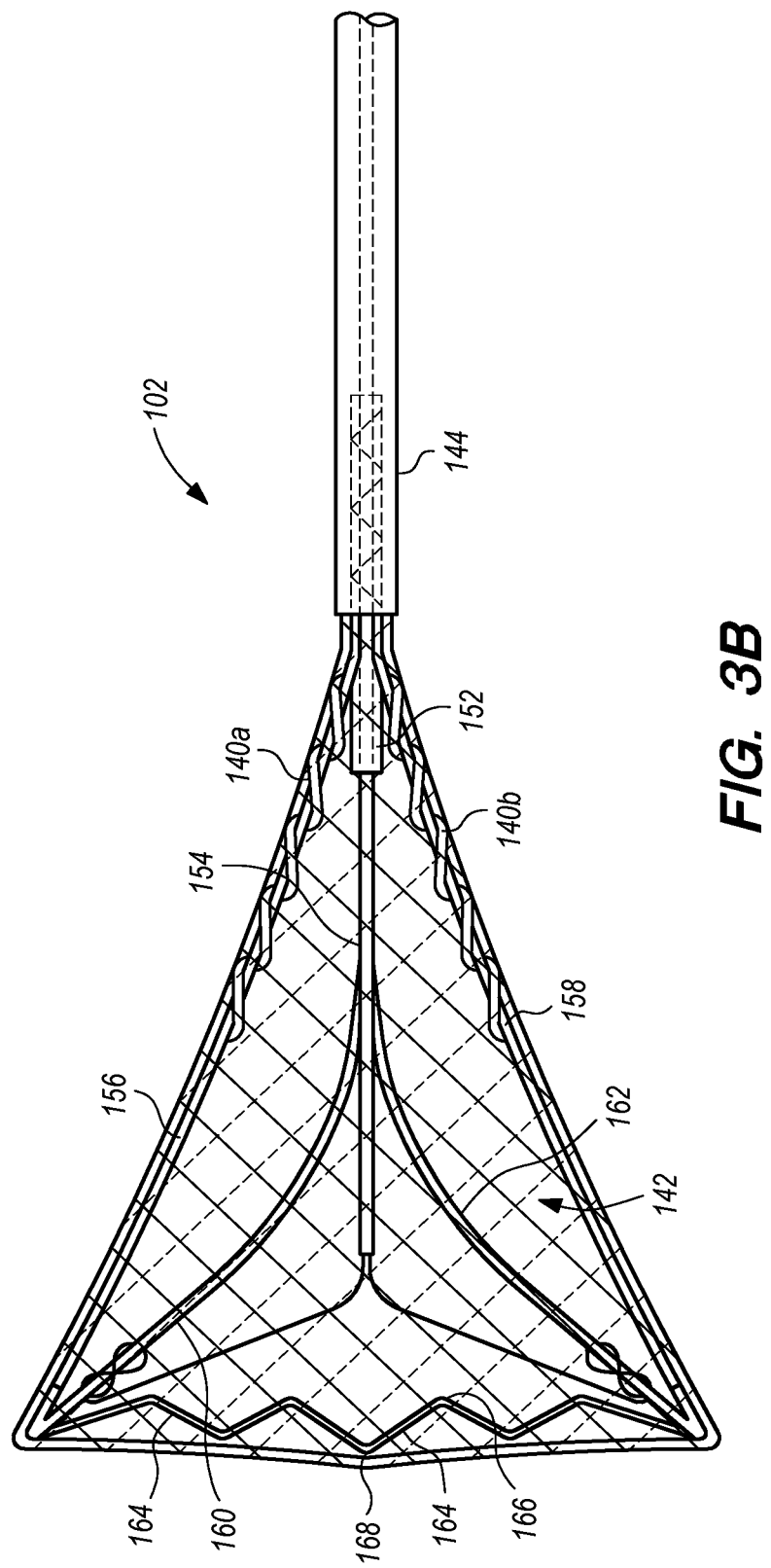
FIG. 3B is an elevation view of an embodiment of an intrauterine therapy application device applicator in a deployed position, according to aspects of the invention.

Referring to FIG. 3A, the intrauterine therapy application device 100 can be spread open by driving an internal central support member 154 forward relative to an external central support member 152. Depending on the forces provided by the drive mechanism used to actuate the internal central support member, the applicator may or may not open to its maximum width. For example, consider using a screw drive to drive forward the internal central support member 154 and to spread the internal 160, 162 and external 156, 158 flexures. The travel of the central support member (and thus the deployment of flexures) is rigidly coupled to the travel of the screw drive. Even if some mechanical restriction prevents the internal and external flexures from spreading to their full width, the screw drive will continue to try to advance the internal central support member. One disadvantage is that this screw drive can generate significant spreading force in the flexures, and it can result in heavy stress on the flexures.

As a second example, consider introducing a compliant element, such as a spring, between the screw drive and the internal central support member 154. The spring transmits force from the screw drive to the internal central support member, so that if the external flexures are unrestricted, the flexures will deploy normally to their full width. Alternatively, in the event that the tips of the flexures somehow become restricted, the spring can absorb the screw's travel, allowing the flexures to rest at a sub-maximum width without heavy stress. Thus, the introduction of a compliant element between the screw drive and the internal support member allows for a simple drive mechanism that drives a deployment mechanism that can automatically open to variable maximum widths (i.e. opening to fill a cavity of unknown size). It also controls the spreading force that the deployment mechanism is able to generate.

Functionally, the purpose of the deployment mechanism of the intrauterine therapy application device is to spread the mesh array 142 from a collapsed state into a deployed state. The mesh array is knit from elastic yarn, so a certain level of force is needed simply to spread the mesh array to the desired shape. On top of stretching the mesh array, the deployment mechanism must be capable of generating additional spreading force to ensure that the deployment mechanism still opens properly if resistance is encountered. Simultaneously, it is desirable for the deployment mechanism to be as small as possible and to be as mechanically durable as possible.

One approach considered by the Applicants for a deployment mechanism used internal flexures made of a single-thickness piece of material. These single-thickness internal flexures had a relatively consistent stiffness and, therefore, a relatively consistent bending radius. The resulting deployed shape of the internal flexure was approximately an arc. For most scenarios, this single-thickness internal flexure provided a structure that was sufficiently mechanically durable. However, this arc can be susceptible to damage under mechanically disadvantageous loading conditions. There are a few solutions that were considered to reduce this susceptibility.

A first approach to improving the durability of the deployment mechanism is that the strength of the internal flexure could be increased so that a greater mechanical stress would be required to damage the internal flexure. One way to do this would be to add material to the internal flexure, either increasing the thickness or height of the internal flexure. However, a drawback of this approach is that it would increase the overall size of the deployment mechanism. Additionally, increasing the thickness of the internal flexure could increase the rigidity of the internal flexure so much that it would be unable to conform to the desired arc profile without permanently deforming.

A second approach to improving the durability of the deployment mechanism is to make the entire internal flexures more compliant/resilient so that the deployment mechanism can endure significant mechanical manipulation and displacement without undergoing permanent deformation. This approach could be achieved, for example, using either a thinner or lower-height internal flexure, by selecting a more flexible material for the internal flexures, or decreasing a width of the entire internal flexures. While this approach could reduce the size of the deployment mechanism, the reduction in the resilience of the entire flexures of the deployment mechanism can be a problem. Applicants discovered that prototypes with such compliant flexures though flexible and resilient, lacked the mechanical strength needed to sustain the desired spreading forces and deploy the mesh array. Applicants discovered that prototypes with such compliant flexures result in decreased integrity of the deployment mechanism of the applicator and an increased chance of buckling of the deployment mechanism of the applicator during deployment from the sheath and/or collapsing of the applicator. When an applicator buckles, the flexures of the deployment mechanism bend at an unintended angle and may lead to an overall shape of the deployment mechanism and the applicator being compromised. A further disadvantage of such modified flexures and deployment mechanism is that the buckling of the applicator may also lead to difficulty or inability to retract the applicator into its sheath or expand the applicator into its expanded position.

To generate adequate spreading forces in a smaller, sufficiently robust deployment mechanism, Applicants discovered a more complex approach that solves the above-noted issues. Specifically, Applicants discovered that it is desirable for a distal portion of the internal flexures to be made stronger, but for the internal flexures to still be capable of bending enough to generate sufficient lateral spreading of the mesh array. One solution considered was a strong, rigid internal flexure, connected by a hinge to the central support member. But a robust hinge would be difficult to fit in such a small space and therefore was not used. Another solution is to build a living hinge into the internal flexure. This structure and arrangement has the advantages of being compact, strong, and favorable from a manufacturing perspective. Ultimately, with such a structure and arrangement, the same array spreading performance and improved mechanical durability can be delivered in a smaller package than a single-thickness flexure design. The performance improvement of this deployment mechanism is most noticeable when the deployment mechanism is actuated by the compliant drive mechanism described earlier.

Referring now to the Figures, a detailed description of various embodiments of such an intrauterine therapy application device, deployment mechanism, and applicator structure will now be discussed. FIG. 1 is a side elevation view of an intrauterine therapy application device 100 with an applicator 102 in a retracted position inside a hollow sheath 104. The intrauterine therapy application device 100 includes a handle 106, and is coupled via a cable 120 to a radiofrequency signal generator 110 and via a tube 128 to a vacuum source 112. The radiofrequency generator 110 generates an electrical signal, for example a radiofrequency signal, and transmits it to the applicator 102 through the cable 120, which is ultimately coupled to the applicator through the handle 106. The vacuum source 112 is connected to the handle 106 at the vacuum port 122 and creates suction in the distal end of the applicator 102. According to one feature, the distal end 104a of the sheath 104 of the intrauterine therapy application device 100 is configured to be inserted into a patient's cervix.

Figure 2:
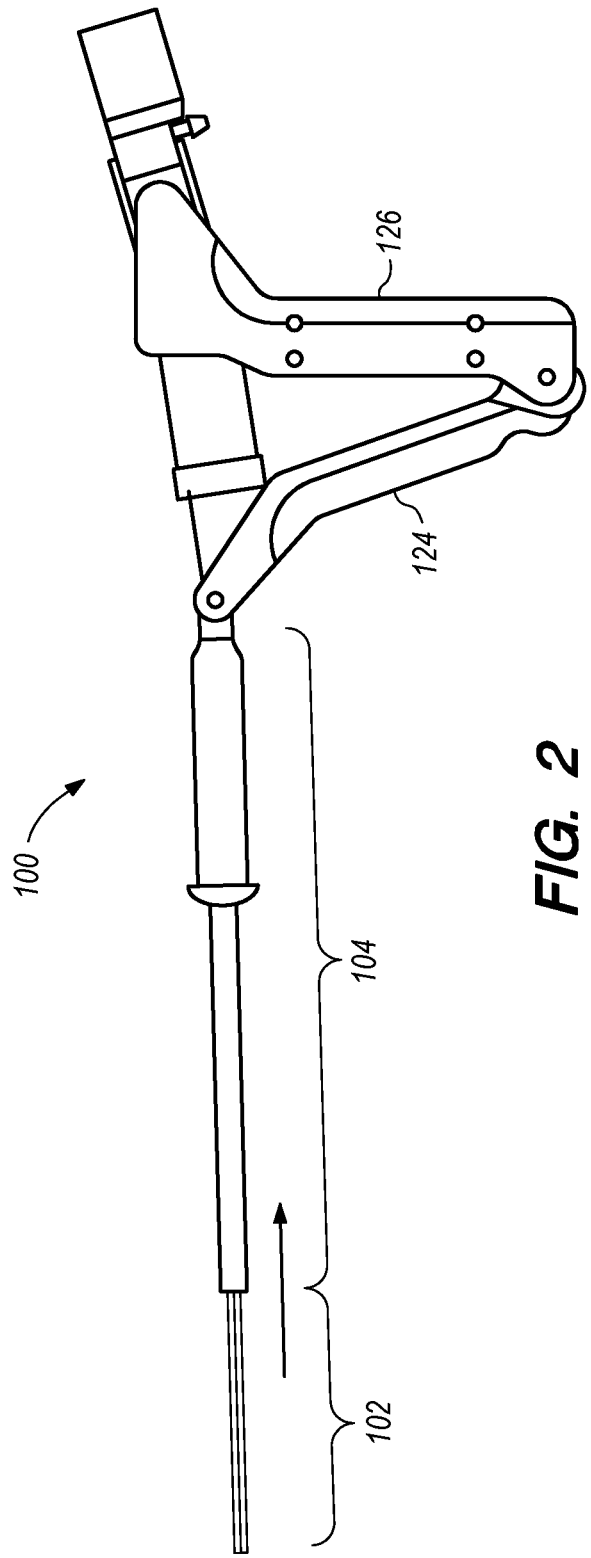
FIG. 2 is a side elevation view of the intrauterine therapy application device of FIG. 1, showing the applicator in a deployed position according to aspects of the invention.

The handle 106 includes a distal grip 124 and a proximal grip 126. During use, the proximal grip 126 is squeezed toward the distal grip 124, to cause the applicator 102 to extend out from the sheath 104, as shown in FIG. 2. As shown in FIG. 2, the applicator 102 is extended out from the sheath 104 in a collapsed position. As the applicator 102 extends out from the sheath 104 in the collapsed position, it also expands as shown in the perspective view of the deployed applicator illustrated in FIGS. 3A and 3B.

FIG. 3A is a perspective view of a portion of an intrauterine therapy application device applicator 102 in a deployed position, according to an embodiment of the invention. The applicator 102 includes an external central support member 152, an internal central support member 154, external flexures 156 and 158 and internal flexures 160 and 162. The proximal end of the internal central support member 154 is coupled to the distal end of the external central support member 152, so as to provide a telescoping arrangement. The proximal ends 156a and 158a of the external flexures 156 and 158 are attached to the outside of the external central support member 152 near the distal end of the external support member 152. The proximal ends 160a and 162a of the internal flexures 160 and 162 are attached to the outside of the internal central support member 154, near the proximal end of the internal central support member 154. It is to be appreciated, as will be discussed below for example with respect to FIGS. 14-16 that in other embodiments, the proximal ends 160a and 162a of the internal flexures 160 and 162 may be attached to the inside of the internal central support member 154, or the proximal ends 160a and 162a of the internal flexures 160 and 162 may be attached into the wall of the internal central support member 154. The external flexures 156 and 158 and the internal flexures 160 and 162 are attached to the external 152 and internal 154 support members such that the external flexures 156 and 158 and internal flexures 160 and 162 flexures lie in the same plane.

The external flexures 156 and 158 in one position extend outward away from being parallel with the central support members 152 and 154 to form a V-shape. According to one embodiment, the external flexures 156 and 158 extend laterally away from the external central support member 152, flaring outwards toward the distal ends 156b and 158b. Similarly, the internal flexures 160 and 162 extend laterally away from the internal central support member 154, forming a flared V-shape. The second sections 160b and 162b of the internal flexures 160 and 162, adjacent to the proximal ends 160a and 162a, gradually extend laterally away from the internal central support member 154. A third section 160c and 162c of each internal flexure 160 and 162 extends substantially laterally and longitudinally away from the internal central support member 154. The distal end 160d of the first internal flexure 160 is attached to a distal end 156b of the first external flexure 156, and a distal end 162d of the second internal flexure 162 is attached to the distal end 158b of the second external flexure 158.

As shown in FIG. 3A, the central support member of the device applicator 102 includes external central support member 152 coupled internal central support member 154.

In other embodiments, the applicator 102 may include three or more support members coupled together. The external 152 and internal 154 central support members may move relative to one another. In one example, the external 152 and internal 154 central support members may be telescoping support members. In another example, the external 152 and internal 154 central support members may be slidably coupled together.

According to aspects of the device, a transverse ribbon 164 can extend between the distal ends 156b and 158b of the external flexures 156 and 158. In one embodiment, the transverse ribbon has a corrugated shape, and includes a plurality of creases 166 and 168, such that when the intrauterine device 102 is in the collapsed position, as shown in FIG. 4, the transverse ribbon 164 is folded along the creases 166 and 168.

Referring back to FIG. 3A, according to one embodiment, the external central support member 152 and the internal central support member 154 are hollow elongate tubes. When a suction is applied to the applicator 102, for example from the suction source 112 shown in FIG. 1, fluid, vapor, liquid, and/or tissue may be suctioned through hollow elongate tubular internal support member 154, away from the patient.

According to one aspect, the external flexures 156, 158 and internal flexures 160, 162 include multiple apertures 172. During use inside a patient, the apertures allow fluid, vapor, liquid and/or tissue to flow through the flexures and move within the uterus. According to aspects of the device, as shown in the illustrative embodiment, the transverse ribbon 164 also includes multiple apertures.

FIG. 3B is a perspective view of the portion of an intrauterine therapy application device applicator 102 in a deployed position and having a mesh array 142, according to an embodiment of the invention. The mesh array 142 surrounds the applicator 102. The mesh array 142 may be knitted from a nylon and spandex knit and plated with gold, silver, or another conductive material. The mesh array 142 is conformable, permeable, and carries current. The mesh array 142 is attached to the external flexures 156, 158 with strands of thread 140a and 140b. The strands of thread 140a, 140b may be nylon. The strands of thread 140a, 140b are sewn through the mesh array 142 and around the external flexures 156, 158. Some examples of a mesh array are described in U.S. Pat. No. 6,813,520 to Truckai et al., which is hereby incorporated by reference herein in its entirety.

FIG. 4 is a perspective view of an intrauterine therapy application device with the applicator 102 illustrated in a collapsed position. In the collapsed position, the external flexures 156, 158 and the internal flexures 160, 162 extend laterally parallel with the external 152 and internal 154 central support members. The transverse ribbon 164 is folded along the creases 166, 168 shown in FIG. 3A. During use of an intrauterine therapy application device, such as the device 100 described with respect to FIG. 1, the applicator 102 is in a collapsed position inside the sheath 104 while the sheath 104 is inserted through the cervix. When the applicator 102 is extended distally from the distal end of the sheath 104, it expands to the deployed position shown in FIG. 3A.

According to features of this disclosure, the internal flexures may be designed to include at least one flexible section adjacent to one or more rigid sections. In one embodiment, a flexible section is positioned between two more rigid sections. The flexible section facilitates bending outward, away from the central support member, allowing the internal flexures to expand laterally away from the central support member to create a V-shape. FIG. 5 is a perspective view of an embodiment of an intrauterine therapy application device applicator 202 showing an internal central support member 204, external flexures 206, 208, and internal flexures 210, 212 having a flexible section and two rigid sections. The first internal flexure 210 and second internal flexure 212 each include at least three sections 210a, 210b, 210c and 212a, 212b, 212c. A proximal section 210a, 212a of each internal flexure is attached to or coupled to the central support member 204 and has a first thickness, a middle section 210b, 212b of each internal flexure has a second thickness, and a distal section 210c, 212c of each internal flexure has a third thickness. According to one embodiment, the second thickness is less than the first thickness and less than the third thickness, so that the middle section 210b, 212b is configured to bend more readily than the respective first and third sections, which facilitates the flexures 210, 212 to angle laterally away from the internal central support member 204. The first sections 210a, 212a and third sections 210c, 212c sections are stiffer than the second sections 210b, 212b. In one embodiment, the first thickness is substantially the same as the third thickness, but it is also contemplated that the first and third thicknesses can be different.

It is to be understood that stiffness refers to the bending characteristics of a flexure. Regions of a flexure that are more resistant to bending are considered to be stiffer, or have a greater stiffness, than regions of a flexure that bend more easily. It is appreciated that several properties of flexure construction can be controlled to adjust stiffness and create a flexure with two or more portions, each having a different stiffness. For example, selected manufacturing processes can be used to alter a material's modulus of elasticity. The manufacturing processes can be used selectively on different areas of a flexure to create a flexure with different moduli of elasticity in different areas of the flexure. In another example, a flexure may be constructed of multiple materials, each material having a different modulus of elasticity. In a further example, the cross-sectional profile of a flexure, such as the thickness and/or width of the flexure may be adjusted to create a flexure having multiple portions, each portion having a different stiffness. Adjusting the cross-sectional profile of the flexure locally alters the flexure's bending moment of inertia, thereby rendering that portion of the flexure either more resistant to bending or less resistant to bending. In further embodiments, other methods and characteristics may be used to control the stiffness of different portions of a flexure.

Figure 6:
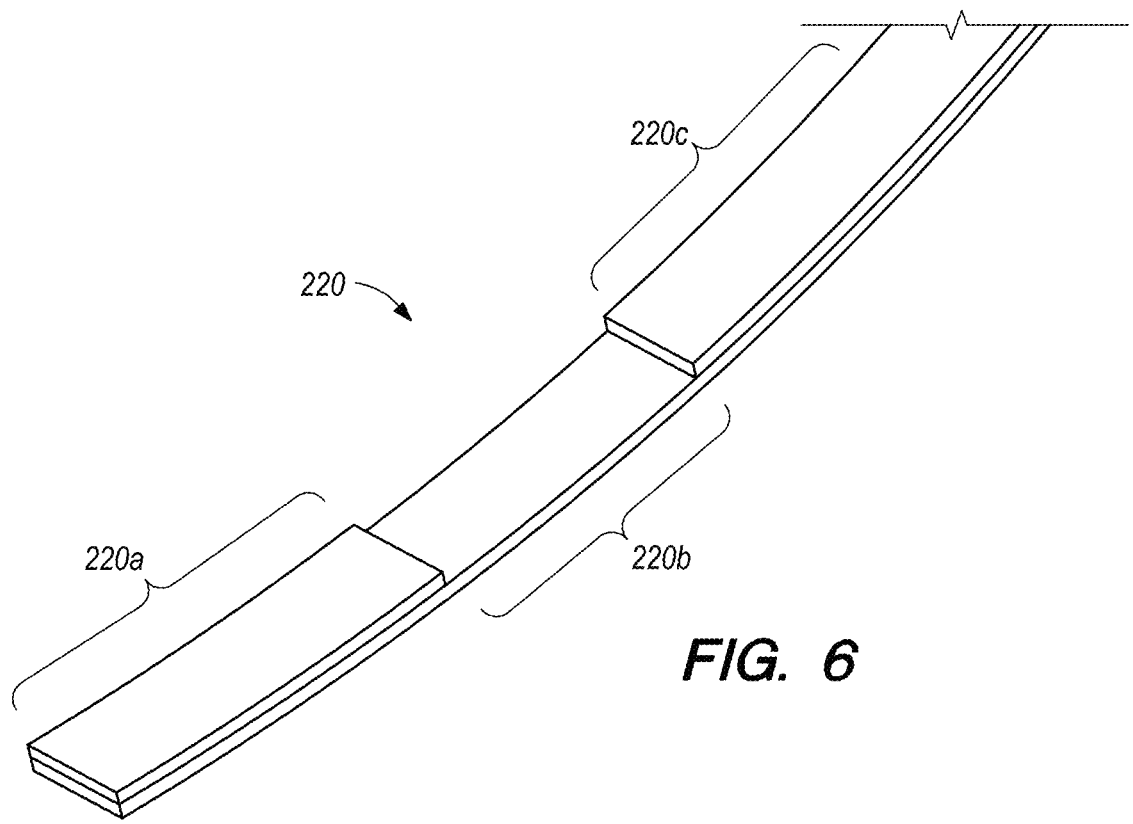
FIG. 6 is a blown up view of an embodiment of a section of an internal flexure having a varying thickness according to aspects of the invention.

FIG. 6 is a blown up top elevation view of a portion of an internal flexure 220 having a varying thickness, according to an embodiment of the invention. As shown in FIG. 6, internal flexure 220 includes a proximal section 220a having a first thickness, a middle section 220b having a second thickness, and a distal section 220c having a third thickness. According to one embodiment, the second thickness is less than the first thickness and the third thickness, and the middle section 220b is configured to bend. For example, when pressure is applied to the distal section 220c of the internal flexure 220, pushing it away from a central support member 204, the internal flexure 220 bends at the middle section 220b because the middle section 220b is less stiff than the distal section 220c. As shown with respect to FIG. 5, the distal sections 210c, 212c of the first internal flexure 210 and second internal flexure 212 remain relatively straight and rigid, while the lateral angling occurs at the middle sections 210b, 212b.

Figure 7:
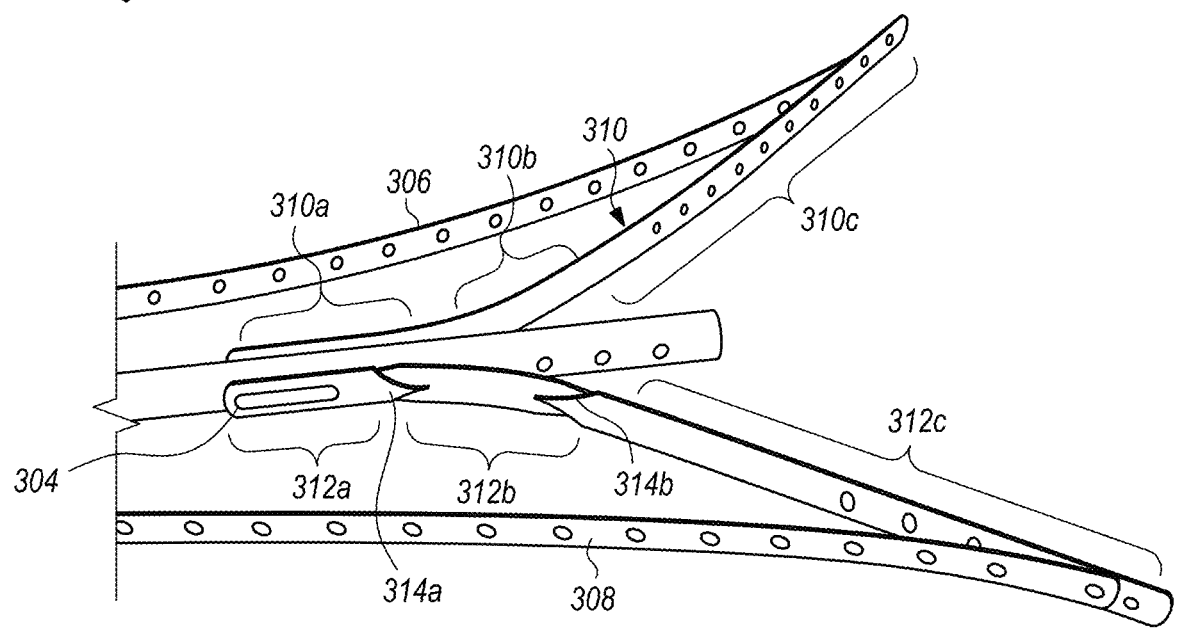
FIG. 7 is a perspective view of an embodiment of a portion of an intrauterine therapy application device applicator showing internal flexures of varying thickness according to aspects of the invention.
Figure 8:
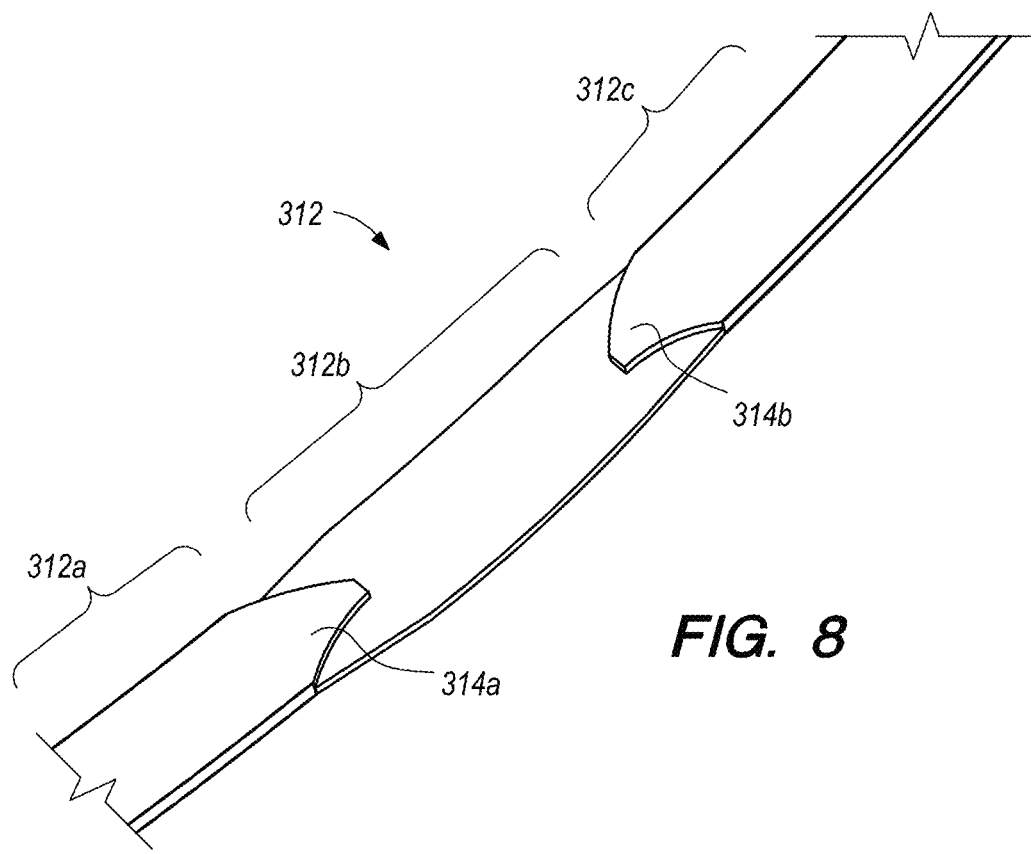
FIG. 8 is a blown up view of an embodiment of a section of an internal flexure having varying thickness according to aspects of the invention.

Referring now to FIGS. 7-8, according to another embodiment, the internal flexures include strain relief portions to decrease the possibility of undesirable bending or breaking. FIG. 7 is a perspective view of an ablation device applicator 302 showing an internal central support member 304, external flexures 306, 308, and internal flexures 310, 312. According to aspects of this applicator, the internal flexures 310, 312 have varying thickness and include strain relief portions. The internal flexures 310, 312 each include a proximal section 310a, 312a, a middle section 310b, 312b, and a distal section 310c, 312c. The proximal sections 310a, 312a and the distal sections 310c, 312c each include strain relief portions 314a, 314b (See also FIG. 8). The strain relief portions 314a, 314b are triangular-shaped portions located at an end of each section 310a, 312a and 310c, 312c where the proximal sections 310a, 312a and the distal sections 310c, 312c attach to the middle section 310b, 312b, as described in greater detail below with respect to FIG. 8.

FIG. 8 is a blown up view of a portion of internal flexure 312 having varying thickness and strain relief portions 314a, 314b according to an embodiment of the invention. The internal flexure 312 includes proximal section 312a, middle section 312b, and distal section 312c. A distal end 314a of the proximal section 312a has a triangular shape and acts as a strain relief to relieve stress at the interface between the proximal section 312a and the middle section 312b. A proximal end 314b of the distal section 312c similarly has a triangular shape and acts as a strain relief to relieve stress at the interface between the distal section 312c and the middle section 312b. It is appreciated that in other embodiments, the strain relief portions 314a, 314b may be other shapes, such as rounded or semi-circular. The middle section 312b is configured to be more flexible than the proximal section 312a and the distal section 312c, such that the internal flexure 312 bends along the middle section 312b.

According to the embodiment of FIG. 8, the proximal section 320a has a first thickness, the middle section 320b has a second thickness, and the distal section 320c has a third thickness. According to one feature, the second thickness is less than the first thickness and the second thickness is also less than the third thickness. It is contemplated that the first thickness and the third thickness can be substantially the same thickness or different thickness.

According to another embodiment, the proximal section 312a has a first width, the middle section 312b has a second width, and the distal section 312c has a third width. According to one feature, the second width is narrower than the first width, and the second width is narrower than the third width. It is contemplated that the first width and the third width can be substantially the same or different. It is to be appreciated that alternate embodiments can easily be provided where the second section is wider than the first and third sections.

Referring to FIG. 7, similar to the internal flexures 210-212 illustrated in the embodiment of FIG. 5, the internal flexures 310, 312 include at least one flexible section positioned between two stiffer sections. The flexible section is configured to bend outward, away from the central support member, allowing the distal end of the internal flexures to expand laterally away from the central support member to create a V-shape. According to one embodiment, the second sections 310b, 312b are configured to bend, allowing the internal flexures 310, 312 to angle laterally away from the internal central support member 304. The first sections 310a, 312a and third sections 310c, 312c are stiffer than the second sections 310b, 312b. The second sections 310b, 312b are more flexible so as to facilitate bending at the second sections 310b, 312b. In one example, the first sections 310a, 312a and third sections 310c, 312c are rigid or substantially rigid.

Figure 9A:
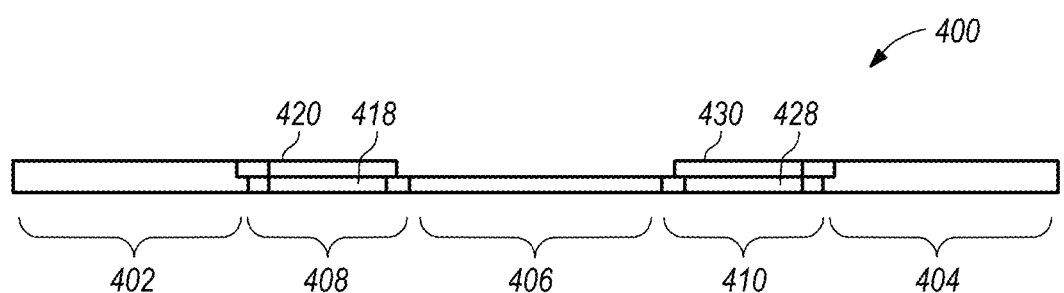
FIG. 9A is a side view of a section of an embodiment of an internal flexure having varying thickness according to aspects of the invention.

FIG. 9A is a side view of a section of an internal flexure 400 having varying thickness, according to an embodiment of the invention. The internal flexure 400 has at least two different thicknesses. In particular, a thickness of the middle section 406 is less than a thickness of the rest of the flexure 400. It is contemplated that the rest of the flexure can have substantially the same or different thicknesses. In the illustrated embodiment, the proximal 402 and distal 404 sections of the flexure 400 have substantially the same thickness, and the first transition area 408 and second transition area 410 have substantially the same thickness as the proximal 402 and distal 404 sections. In one example, the transition areas 408 and 410 are welded to the section 406. It is to be appreciated that the areas of different thickness can also be provided by other structures. For example, each of the transition areas 408 and 410 may be etched together, such that each transition area 408 and 410 is a single piece of material. In another example, the entire flexure 400 is etched as a single piece of material. In a further example, the transition areas 408 and 410 each include two layers of stacked material that are bonded together by various techniques known in the art. For example, the first transition area 408 includes a first bottom layer 418 and first top layer 420, and the second transition area 410 includes a second bottom layer 428 and second top layer 430. In some embodiments, the internal flexure 400 may include additional transitional areas between the middle section 406 and the proximal section 402 and distal section 404.

Figure 9B:
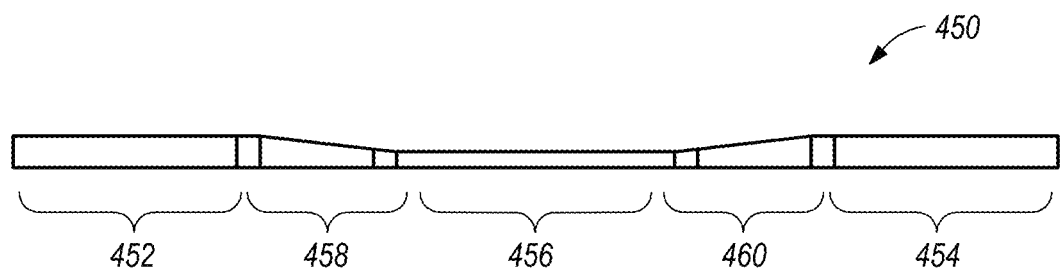
FIG. 9B is a side view of a section of an embodiment of an internal flexure having varying thickness according to aspects of the invention.

For example, FIG. 9B is a side view of a section of an internal flexure 450 having two tapering thickness sections 458, 460, according to another embodiment of the invention. In this embodiment, a thickness of a middle section 456 is less than a thickness of the rest of the flexure 450, and a thickness of the proximal section 452 and a thickness of the distal section 454 is greater than the thickness of the rest of the flexure 450. It is contemplated that the thickness of the proximal section and the distal section can be the same or different. The internal flexure also includes a first transitional region 458, positioned between the proximal section 452 and the middle section 456, which has a varying thickness that tapers from the thickness of the proximal section 452 to the thickness of the middle section 456. Similarly, the second internal flexure also includes a transitional region 460, positioned between the distal section 454 and the middle section 456, which has a varying thickness that tapers from the thickness of the distal section 454 to the thickness of the middle section 456.

It is to be appreciated that varying the thicknesses of the internal flexure 400 of FIG. 9A and the internal flexure 450 of FIG. 9B provides for the overall diameter of the intrauterine device applicator in a collapsed position to be decreased, while maintaining its strength and stiffness. Decreasing the overall diameter in a collapsed position, of the applicator allows for use of a smaller-diameter sheath. A sheath with a smaller outer diameter may also reduce patient discomfort, and also decrease the potential for cervical injury during insertion. Thus, one advantage of the varying thicknesses of the internal flexures 400 and 450 is that they provide for the outer diameter of the applicator to be decreased, while maintaining the reliability of the deployment of the applicator from the sheath and the retraction of the applicator back into the sheath.

Figure 10:
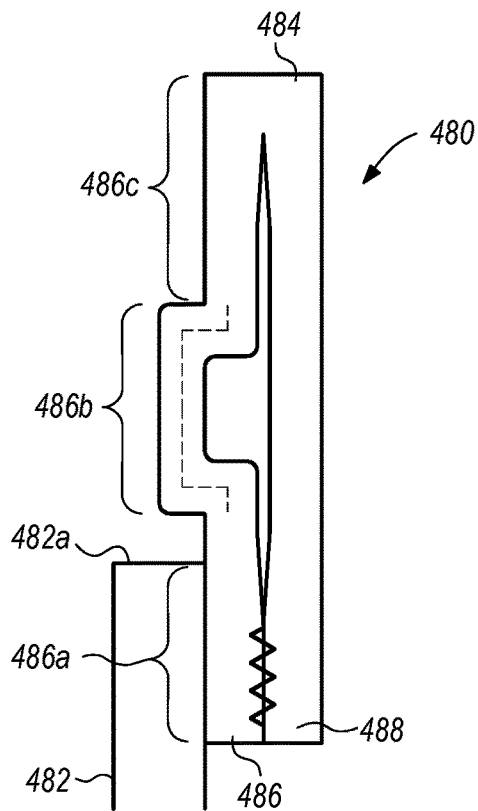
FIG. 10 is a side elevation view of a portion of an embodiment of an intrauterine therapy application device applicator according to aspects of the invention.

FIG. 10 is a side elevation view of another embodiment of a portion of an intrauterine therapy application device 480, including a central support member 482 and an internal flexure 484 having a first section 486 and a second section 488. According to aspects of the disclosure, it may be desirable to control both the lateral and vertical flexibility of the internal flexures of the applicator. This can be accomplished with the internal flexure 484 of FIG. 10. The first section 486 is attached to the central support member 482 and the second section 488 is attached to a proximal portion 486a of the first section 486 and extends parallel to the first section 486. The first section 486 includes a middle portion 486b, positioned just past the distal end 482a of the central support member 482. The middle portion 486b of the first section 486 curves inward away from the second section 488 of the internal flexure 484, extends longitudinally, parallel to the second section 488 but positioned a distance away from the second section 488, and then curves back toward the second section 488 of the internal flexure 484. The distal portion 486c of the first section 486 of the internal flexure 484 is attached to the second section 488 of the internal flexure 484. According to one feature, the shape of the first section 486, including the curved middle portion 486b, increases the durability and reliability of the internal flexure 484.

Figure 11B:
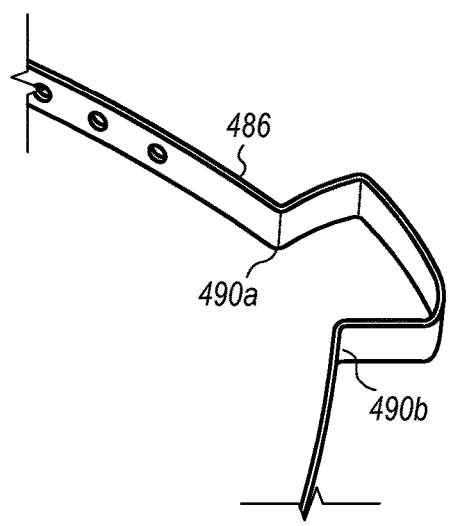
FIGS. 11A-11B show a section of an the internal flexure according to aspects of the invention.
Figure 11A:
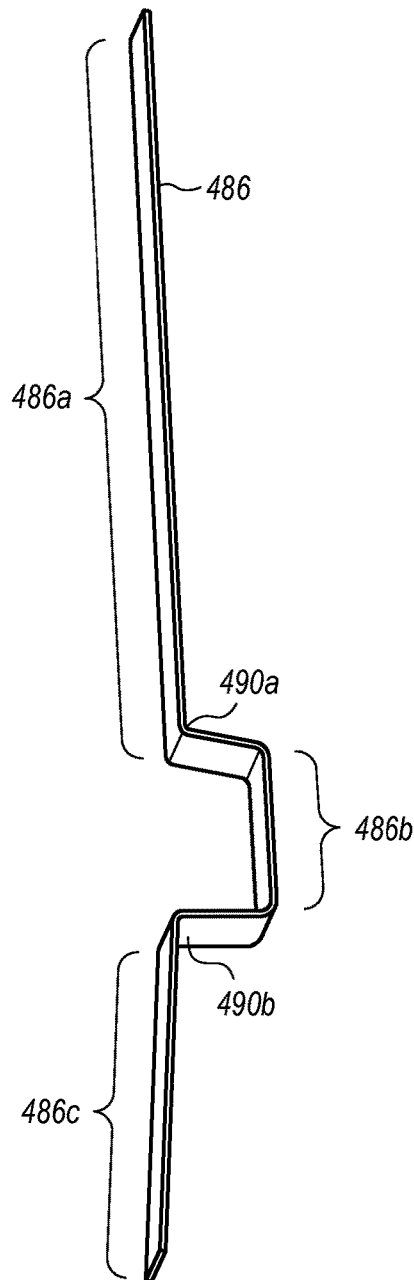

FIG. 11A shows the first section 486 of the internal flexure 484 in a relaxed position and FIG. 11B shows the first section 486 of the internal flexure 484 in an expanded position. According to one feature, the jog in the middle portion 486b of the first section 486 isolates the flexibility and rigidity of the first section 486 to selected parts of the first section 486 of the flexure. For example, first bend 490a and second bend 490b provide areas of flexibility.

Figure 12:
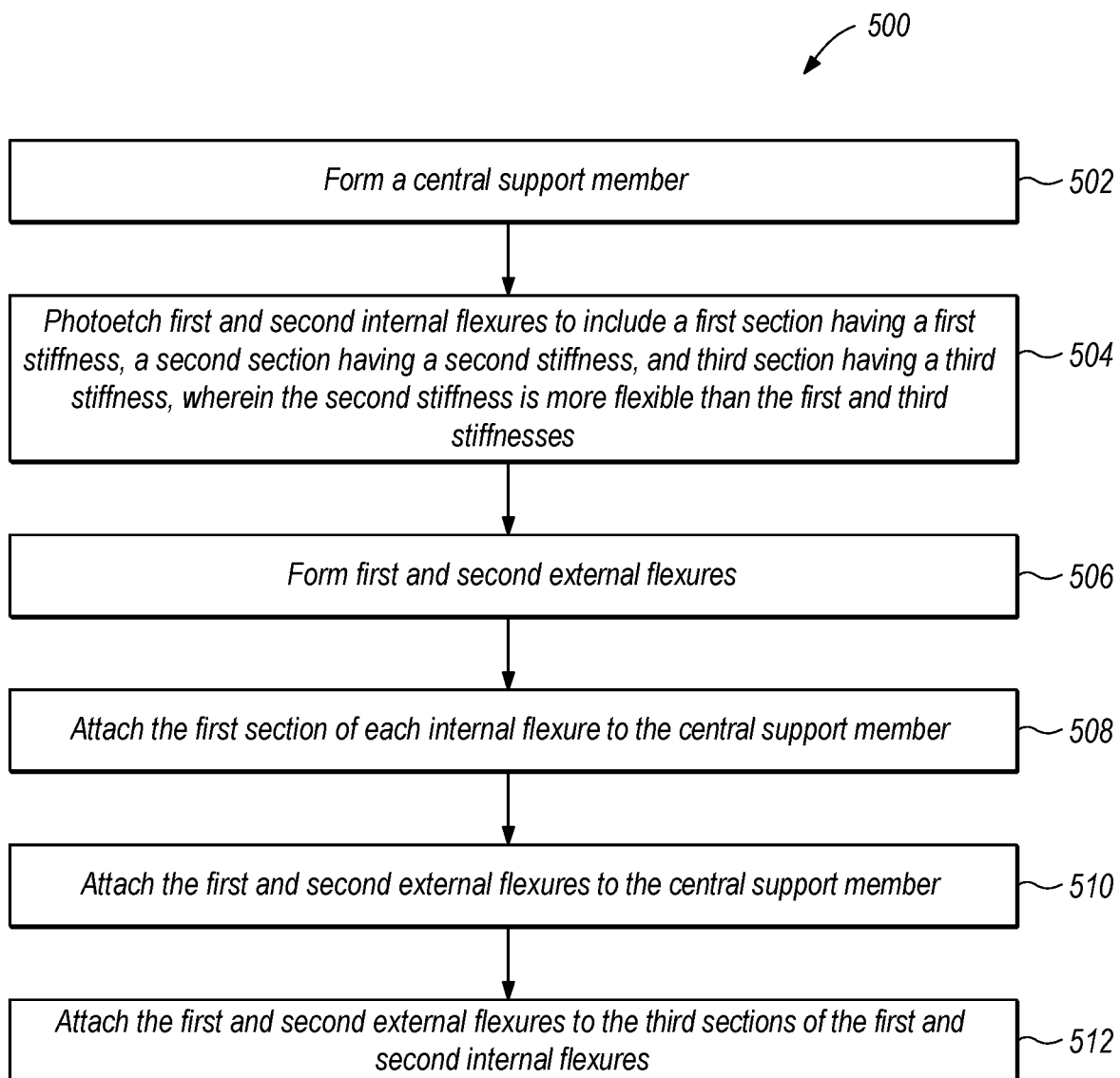
FIG. 12 is a flow chart of a method of manufacturing an intrauterine therapy application device applicator, according to aspects of the invention.
Figure 13:
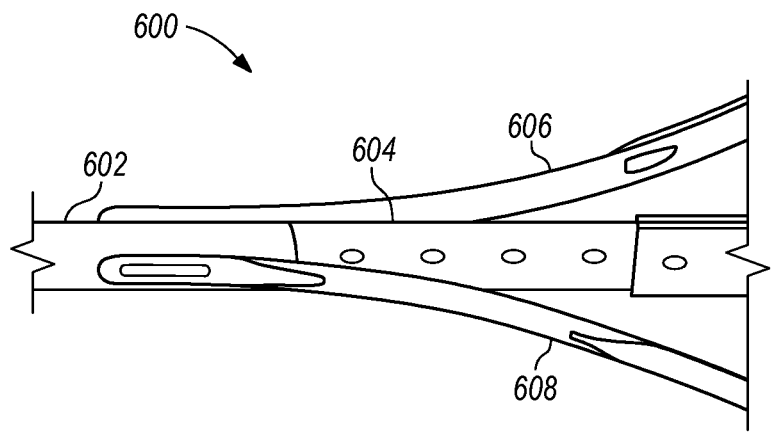
FIG. 13 is a perspective view of an embodiment of an intrauterine therapy application device applicator showing a portion of internal flexures according to aspects of the invention.

In one example, each of the stacked sections 486, 488 is half the thickness of an internal flexure without such stacked sections, so that the thickness of the internal flexure 484 is about the same as the thickness of a single-layer internal flexure. For example, the internal flexure 484 can be a substitute for the internal flexures 160, 162 of FIG. 3A. According to one feature, the internal flexure 484 formed from two stacked sections 486 and 488 has a decreased lateral stiffness compared to an internal flexure formed from a single layer. According to another feature, the internal flexure 484 formed from two stacked sections 486 and 488 has about the same vertical stiffness as an internal flexure formed from a single layer. Thus, the internal flexure of FIG. 10 has a decreased lateral stiffness and a vertical stiffness that is about the same as the internal flexure of the embodiment of FIG. 3A FIG. 12 is a flow chart showing one embodiment of a method 500 of manufacturing an intrauterine device. At step 502, a central support member is provided. At step 504, first and second internal flexures are formed using a photo etching (or photochemical machining) process. The first and second internal flexures include a first section having a first stiffness, a second section having a second stiffness, and a third section having a third stiffness, with the second stiffness more flexible than the first and third stiffnesses, according to the various embodiments discussed herein.

In one example, the photo etching process includes printing the shape of one or more internal flexures onto optically clear and dimensionally stable photographic film. The photographic film shows a negative image of the internal flexures, such that the areas to be etched are black, and the area that will become the internal flexures are clear. Generally, two sheets of photographic film are used. The two sheets are optically and mechanically registered to form the top and bottom halves of the part to be etched (the internal flexure).

Metal sheets for etching into internal flexures are cut to size, cleaned and then laminated on both sides with a UV-sensitive photoresist. A coated metal sheet is placed between the two sheets of photographic film. A vacuum is created to ensure intimate contact between the photographic film and the coated metal sheet. The coated metal sheet is then exposed in UV light that allows the areas in the clear sections of the photographic film to be hardened. After exposure, the plate is developed by washing away the unexposed resist, leaving the areas to be etched unprotected.

An etchant is sprayed on both sides of the developed plate, causing the unprotected areas of the plate to corrode away, leaving the photo etched internal flexures. The etchant may be an aqueous solution of acid, such as ferric chloride. In one example, before spraying the etchant on the developed plate, the etchant is heated. The etching process may take place in a multi-chambered machine that has driven-wheel conveyors to move the plates and arrays of spray nozzles above and below the plates. According to one feature, the top and bottom of the developed plate can be etched at different rates. In one example, etching the top and bottom of the developed plate at different rates allows for better control over the thickness of the resulting internal flexures, and allows for better control over the thickness of the flexible section of the internal flexures. After etching the developed plate, it is neutralized and rinsed, the remaining resist is removed, and the sheet of internal flexures is cleaned and dried. According to various embodiments, the photo etching process described above may be used to form any part of the intrauterine device.

Still referring to FIG. 12, at step 506, the first and second external flexures are provided. The first and second external flexures may be formed using a photo etching process as described above with respect to forming the first and second internal flexures. At step 508, a first section of each internal flexure is attached to the central support member. At step 510, a proximal end of each of the first and second external flexures is attached to the central support member. At step 512, a distal end of each of the first and second flexures is attached to the third section of the first and second internal flexures. Attachment may be done by any means known to those of skill in the art.

According to another embodiment, a stamping process may be used to form the internal flexures. A stamping process would involve producing a flat pattern of metal using a punch and die method, punching out the selected pattern. The resulting flat piece of metal may be locally deformed using a coining process, which can be used to change the shape of the piece of metal to have a higher bending moment of inertia in selected regions, thereby increasing the stiffness of the selected regions.

Figure 14:
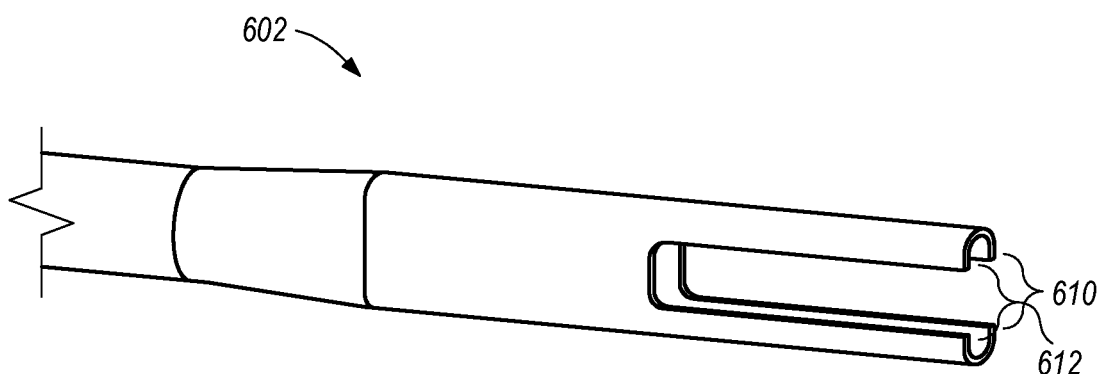
FIG. 14 is an elevation view of a portion of an embodiment of a central support member according to aspects of the invention.
Figure 15:
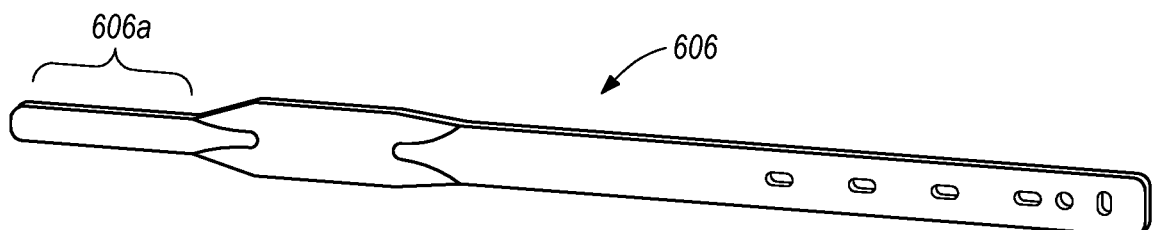
FIG. 15 is an elevation view of a portion of an embodiment of an internal flexure according to aspects of the invention.

FIGS. 13-16 show a portion of another embodiment of a medical device applicator including a notched tubular central support member and mating internal flexures. The intrauterine device applicator 600 includes a tubular proximal central support member 602, internal flexures 606 and 608, and a distal central support member 604. The internal flexures 606 and 608 are inserted into notches in the proximal central support member 602, and welded in place. For example, FIG. 14 shows the proximal central support member 602, including notches 610 and 612. The proximal end of an internal flexure, such as the proximal end 606a of the internal flexure 606 shown in FIG. 15 is inserted into the notches 610, 612 of the central support member 602 shown in FIG. 14. The proximal end of the internal flexure can be secured to the central support member. For example, the internal flexure may be welded to the central support member.

Figure 16:
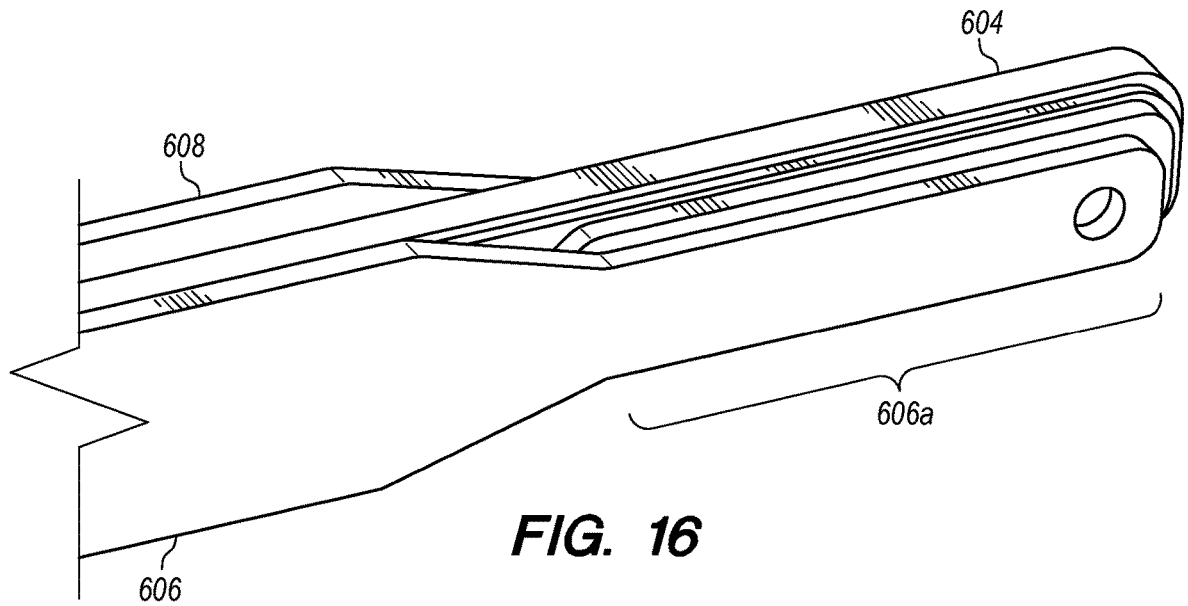
FIG. 16 is a blown up view of a portion of an embodiment of a central support member and internal flexures according to aspects of the invention.

FIG. 16 shows an exploded view of one end of the combination of the distal central support member 604 and the internal flexures 606 and 608. As shown in FIG. 16, the internal flexures 606 and 608 may be coupled to the distal central support member 604. The combination of the internal flexures 606 and 608 and the central support member 604 may be coupled to the proximal central support member 602. For example, the combination t including internal flexures 606 and 608 and the central support member 604 may be inserted into the proximal central support member 602 and secured in place by various techniques known to those of skill in the art.

Figure 17:
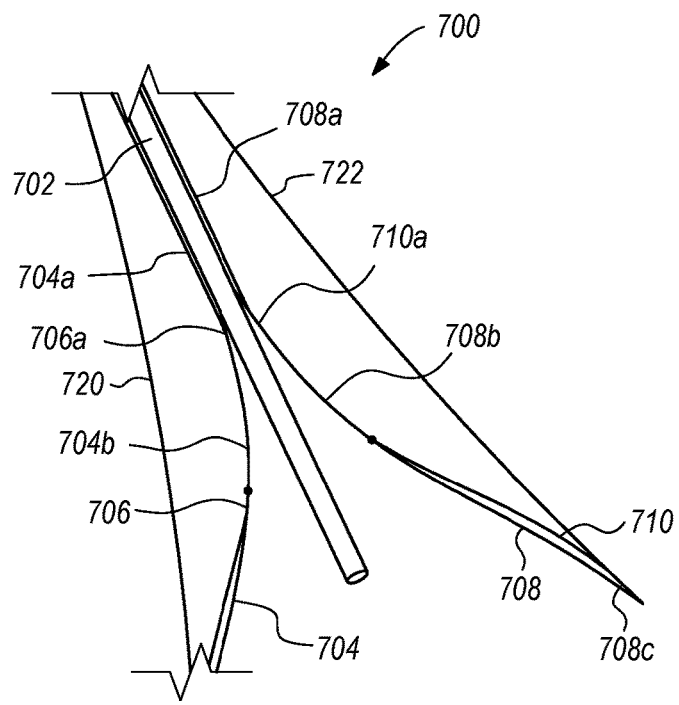
FIG. 17 is a perspective view of an embodiment of an intrauterine therapy application device applicator according to aspects of the invention.

FIG. 17 shows a portion of another embodiment of an intrauterine device applicator 700 having central support member 702, internal flexures 704, 706, 708, and 710, and external flexures 720 and 722. Internal flexures 704, 706 are stacked, and internal flexures 708, 710 are stacked. Internal flexures 704, 708 are joined to the central support member 702 at proximal locations 704a and 708a, respectively, and internal flexures 706, 710 are joined to the central support member 702 at proximal locations 706a and 710a, respectively. Internal flexures 704, 706 are joined to external flexure 720 at a distal location 704c, and internal flexures 708, 710 are joined to external flexure 722 at distal location 708c. As shown in FIG. 17, the stacked pairs of internal flexures 704, 706 can be joined at a middle location 704b. Similarly, internal flexures 708, 710 can be joined at a middle location 708b. It is appreciated that joining methods and structure may include any of welding, tying, bonding, or any other joining method and structure used in the art.

According to one embodiment, the first 704 and second 706 stacked sections are both the same length. For this embodiment, in the deployed state, internal flexure 704 is forced to bend at a slightly different radius than internal flexure 706, causing internal flexures 704, 706 to separate in the distal region, as shown in FIG. 17. It is to be understood that according to this disclosure, this separation behavior is herein referred to as oil-canning. It is to be appreciated that other embodiments as disclosed herein do not exhibit such oil-canning. For example, the embodiments shown in FIGS. 10, 11A and 11B prevent oil-canning by introducing a local compliant region that allows for the end-to-end length of the flexure to change slightly in an intentional manner.

Figure 18:
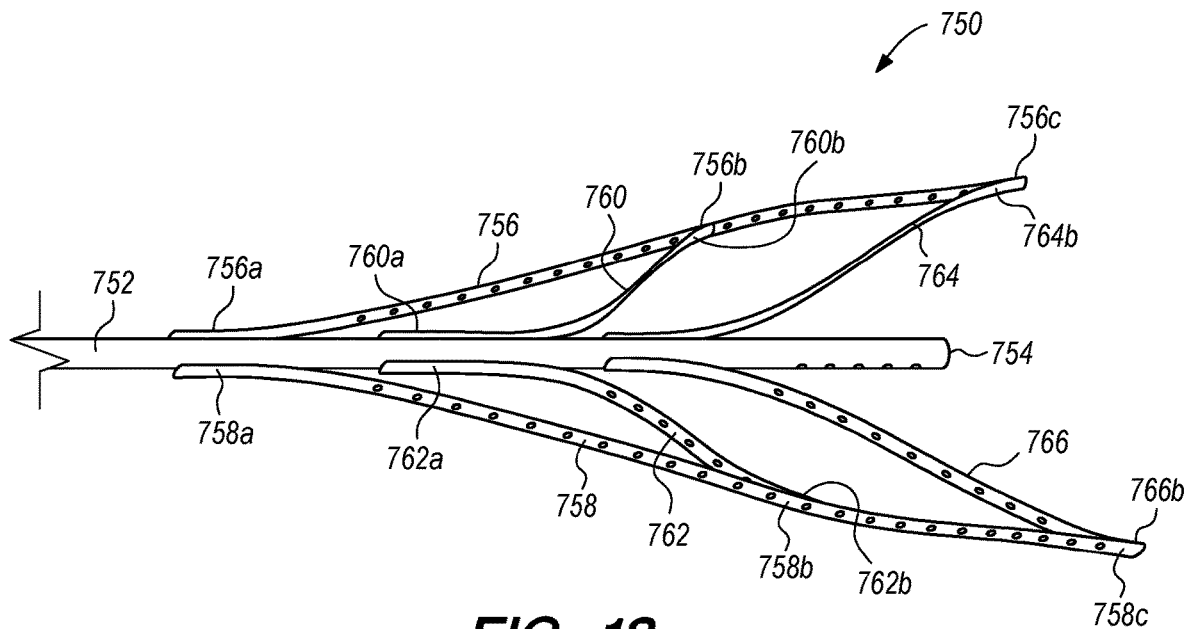
FIG. 18 is a perspective view of an embodiment of an intrauterine therapy application device applicator having two sets of internal flexures according to aspects of the invention.

FIG. 18 shows another embodiment of an intrauterine device applicator 750 having two sets of internal flexures, shown in an expanded position. The intrauterine device 750 includes a proximal central support member 752, a distal central support member 754, external flexures 756, 758, a first set of internal flexures 760, 762 and a second set of internal flexures 764, 766. The proximal ends 760a, 762a of each flexure of the first set of internal flexures 760, 762 are coupled to the distal central support member 754 at a first location 754a. The distal ends 760b, 762b of each flexure of the first set of internal flexures 760, 762 are coupled to a middle portion 756b, 758b the external flexures 756, 758. The proximal ends 764a, 766a of the second set of internal flexures 764, 766 are coupled to the distal central support member 754 at a second location 754b, which second location is distal to the first location. The distal ends 764b, 766b of the second set of internal flexures 764, 766 are coupled to the distal ends 756c, 758c of the external flexures 756, 758. According to one feature, by utilizing three or more flexures and/or strategic location of the joints of the flexures, the shape of the intrauterine device in the expanded position can be controlled to reliably match complex anatomy better than when using a more basic two-flexure design. In one embodiment, the internal flexures 760, 762, 764, 766 each have a thickness about half as thick as the internal flexures 160, 162 shown in FIG. 3A.

According to any of the embodiments disclosed herein, the ribbon 164 shown by way of example in FIGS. 3A-3B may be replaced with alternative mesh support designs. It is appreciated that the ribbon 164 shown in FIGS. 3A-3B takes up a large amount of cross-sectional space in the retracted position, as shown by way of example in FIG. 4. According to various embodiments, FIGS. 19A-B and 20A-C show intrauterine devices with alternative embodiments of arms to support a mesh array. The arms may be used in place of a ribbon to reduce the outer diameter of an intrauterine device in a retracted position. According to various examples, the mesh support arms mechanically support the distal end 818 of the mesh array, preventing the mesh array from pulling back proximally and/or toward the central support members. Additionally, the mesh support arms provide vertical support, mechanically separating the top of the mesh array from the bottom of the mesh array, which may help prevent an alternating current short through the mesh array when energy is delivered to the medical device after it is inserted in a patient.

Figure 19A:
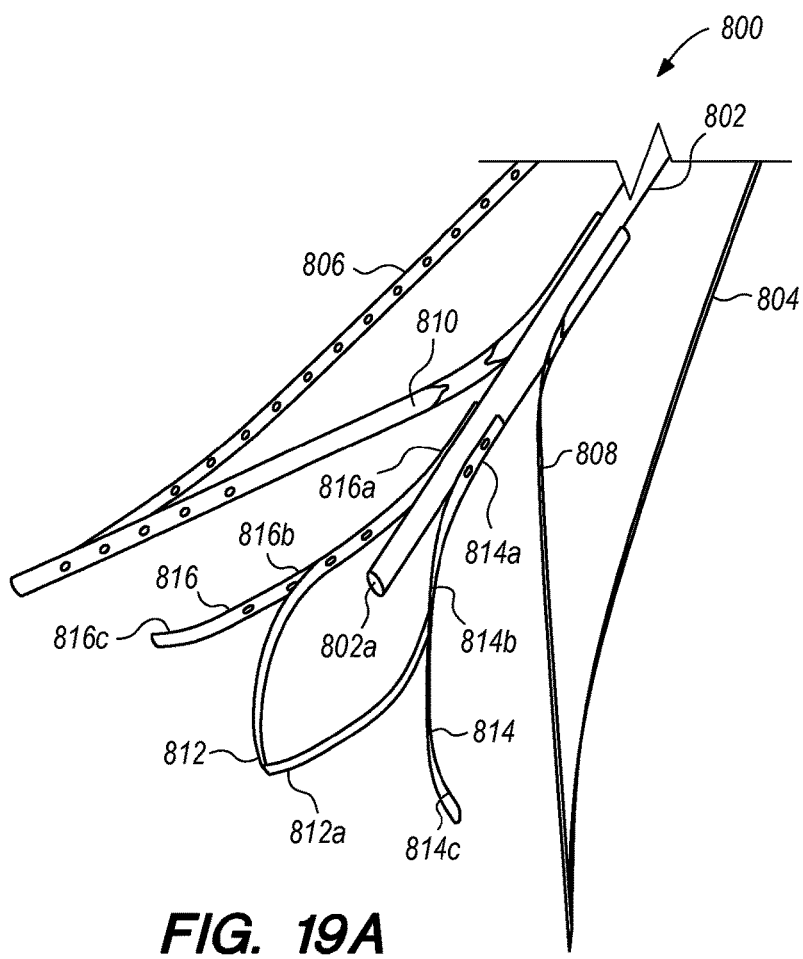
FIG. 19A is a perspective view of a portion of an embodiment of an intrauterine therapy application device applicator, according to aspects of the invention.

FIG. 19A is a perspective view of a portion of an embodiment of an intrauterine ablation device applicator 800 in a deployed position. The applicator 800 includes a central support member 802, external flexures 804, 806, internal flexures 808, 810, arms 814, 816, and a central bridge 812. The proximal ends 814a, 816a of the arms 814, 816 are coupled to the central support member 802, and the arms 814, 816 extend laterally away from the central support member 802. The attachment of the proximal ends 814a, 816a of the arms 814, 816 to the central support member 802 provides flexibility to the arms for lateral extension.

Figure 19B:
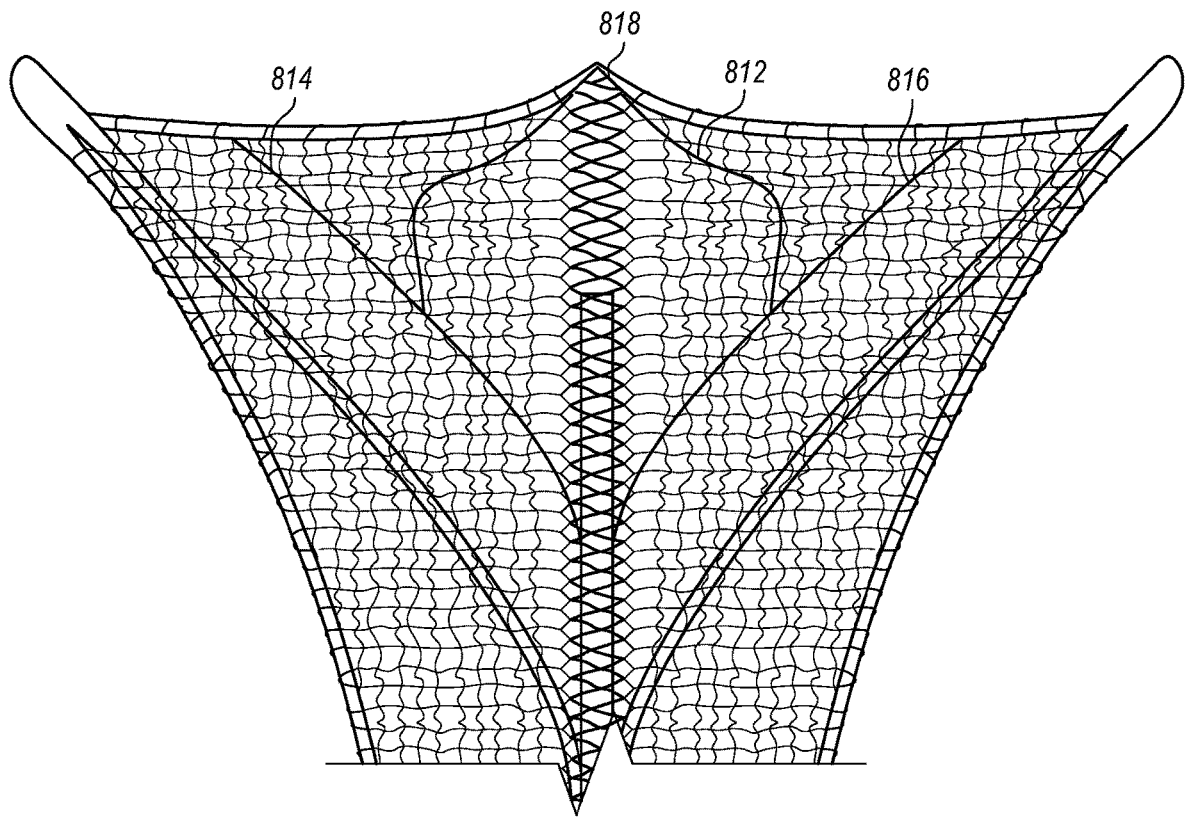
FIG. 19B is an elevation view of a portion of the embodiment of an intrauterine therapy application device applicator of FIG. 19A further including a mesh array, according to aspects of the invention.

As shown in FIG. 19A, each end of a central bridge 812 is coupled to a middle portion 814b, 816b of each arm 814, 816. In an expanded position, the center 812a of the central bridge 812 extends longitudinally beyond the distal end 802a of the central support member 802. When a mesh array is positioned about the intrauterine ablation device applicator 800, as shown in FIG. 19B, the center 812a of the central bridge 812 supports the distal end 818 of the mesh array. According to one embodiment, the arms 814, 816 and the central bridge 812 can be compressed toward the center line of the central support member 802 for retraction into a sheath, such as the sheath 104 of FIG. 1.

According to one feature, attaching the arms 814, 816 to a more proximal location than the distal end of the external flexures, in comparison to where the ribbon 164 of FIG. 3A is attached, results in a device with a smaller outer diameter in a retracted position. In a retracted position, the ribbon 164 of the illustrative embodiment of FIG. 3A is folded multiple times, resulting in eight layers of stacked ribbon material. In contrast, the applicator shown in FIG. 19A includes four layers of arm 814, 816 and central bridge 812 material in the retracted position to provide a reduced diameter in the retracted position. According to one embodiment, the arms 814, 816 and the central bridge 812 are coated in an electrically insulating coating, such as parylene. The coating on the surfaces of the arms 814, 816 and the central bridge 812 increases the thickness of the arms 814, 816 and the central bridge 812 (or, when used on the applicator 102, increases the thickness of the folded ribbon 164).

Figure 20A:
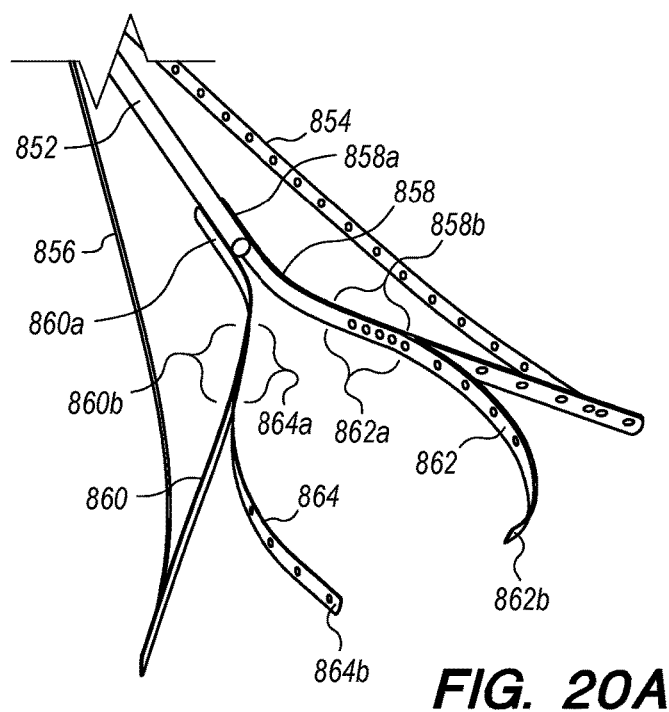
FIG. 20A is a perspective view of a portion of an embodiment of an intrauterine therapy application device applicator, according to aspects of the invention.
Figure 20B:
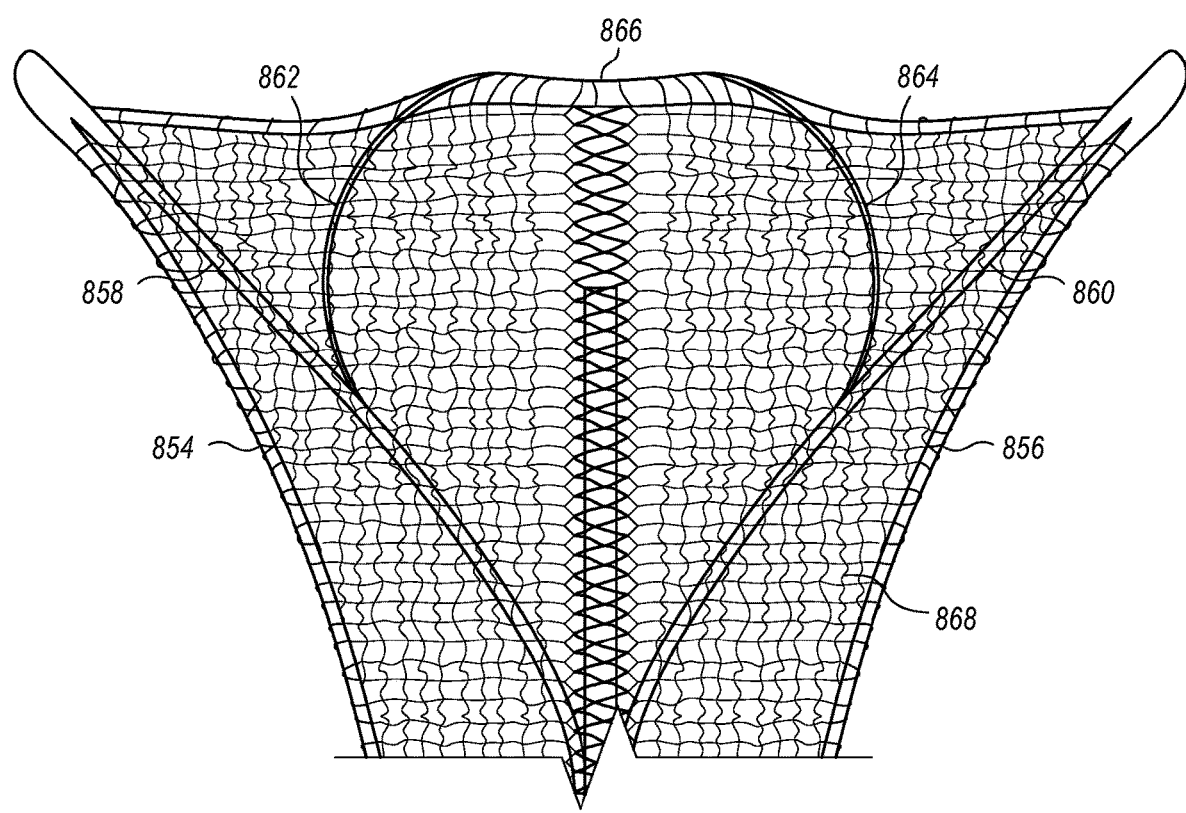
FIG. 20B is an elevation view of a portion of the embodiment of an intrauterine therapy application device applicator of FIG. 20A further including a mesh array, according to aspects of the invention.
Figure 20C:
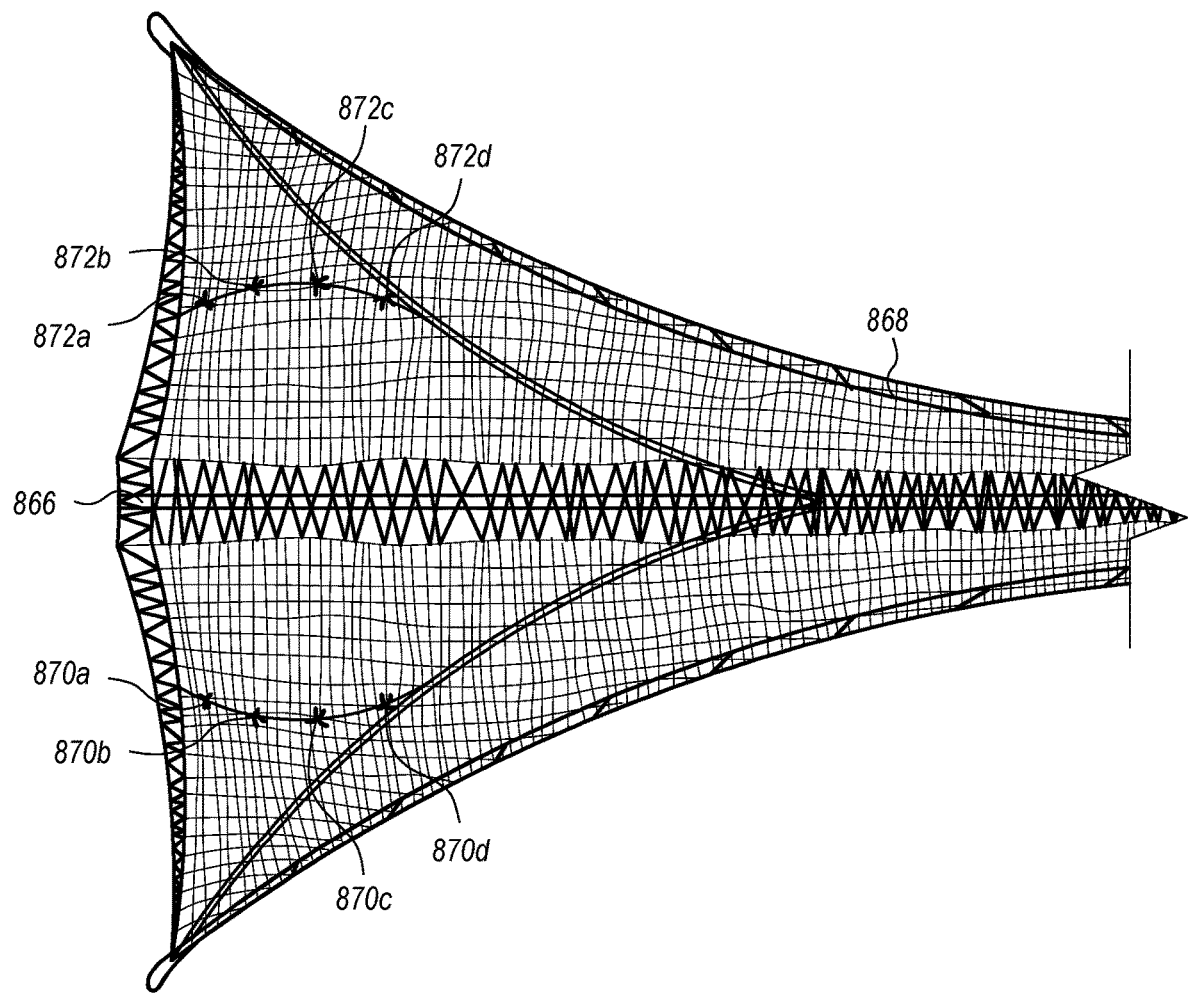
FIG. 20C is an elevation view of a portion of an intrauterine therapy application device applicator having a mesh array, according to aspects of the invention.

FIG. 20A is a perspective view of a portion of another embodiment of an intrauterine ablation device applicator 850 having arms 862, 864 shown in an expanded position. The applicator 850 includes a central support member 852, external flexures 854, 856, internal flexures 858, 860, and arms 862, 864. The proximal ends 862a, 864a of the arms 862, 864 are coupled to a middle portion 858b, 860b of the internal flexures 858, 860. The arms 862, 864 curve laterally outward, and then curve back in toward the center line defined by the central support member 852. The distal ends 862b, 864b of the arms 862, 864 are directed inward toward the center line. FIG. 20B is an elevation view of a portion of the intrauterine ablation device applicator 850 of FIG. 20A with a mesh array cover 868 disposed thereabout. FIG. 20C is an elevation view of a portion of the intrauterine ablation device applicator 850 of FIG. 20A having a mesh array anchored to the arms 862, 864 in multiple locations 870a-d, 872a-d. By anchoring the arms to the array in one or more locations, the system relies on the combined strength of the arms interacting with the array, providing improved mechanical strength and robustness of the system without increasing the size of the arms. According to one feature, the arms 862, 864 prevent the top and bottom parts of the mesh array from coming in contact with one another. According to another feature, the arms 862, 864 prop up the distal end of the mesh array.

As discussed above, decreasing the thickness of the structure that maintains the extension of the mesh array at the distal end of the applicator 852 allows for a decreased outer diameter of a sheath enclosing the applicator 852 in a retracted position. The applicator 852 includes only two arms 862, 864, which are attached to the internal flexures 858, 860 distal to the distal end of the central support member 852. Thus, the applicator 852 can be positioned within a substantially smaller diameter sheath in the retracted position than, for example, the applicator 102 shown in FIGS. 3A, 3B, and FIG. 4.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:
1. An intrauterine ablation device, comprising:
   a central support elongate member;
   an energy applicator operatively coupled to a distal end portion of the central support elongate member, the energy applicator comprising a tissue contacting member and an expandable-collapsible support structure underlying the tissue contacting member, the expandable-collapsible support structure comprising a first flexure having a first flexure distal tip, and a second flexure having a second flexure distal tip, wherein the expandable-collapsible support structure is adjustable between a collapsed configuration in which the first and second flexure distal tips are closely apposed to one another, and an expanded configuration in which the first and second flexure distal tips are spaced apart from one another; and
   a central bridge having a first curved portion and a second curved portion, wherein the first curved portion has a proximal end attached to the first flexure and a distal end attached to a distal end of the second curved portion, the second curved portion having a proximal end attached to the second flexure, wherein the respective proximal ends of the first and second curved portions are coupled to the central support elongate member; and wherein each of the first and second curved portions of the central bridge assumes a continuously curved configuration between their respective proximal and distal ends when the expandable-collapsible support structure is in the expanded configuration.

2. The intrauterine ablation device of claim 1, wherein the central bridge comprises a flexible ribbon or thin flexible membrane.

3. The intrauterine ablation device of claim 1 wherein an outer surface of the central bridge contacts the first flexure and the second flexure.

4. An intrauterine ablation device, comprising:
a central support elongate member configured for transcervical insertion;
an energy applicator operatively coupled to the central support elongate member, the energy applicator comprising a tissue contacting member and an expandable-collapsible support structure underlying the tissue contacting member, the expandable-collapsible support structure comprising a first outer flexure and a second outer flexure, each of the outer flexures having a respective outer surface in lateral contact with an inner surface of the tissue contacting member, and a first inner flexure and a second inner flexure, wherein the expandable-collapsible support structure is adjustable between a collapsed configuration in which the first and second inner flexures are closely apposed to one another, and an expanded configuration in which the first and second inner flexures are spaced apart from one another;
a central bridge having a first curved portion and a second curved portion, wherein the first curved portion has a proximal end attached to a middle portion of the first inner flexure and a distal end coupled to a distal end of the second curved portion, the second curved portion has a proximal end attached to a middle portion of the second inner flexure,
wherein the respective proximal ends of the first and second curved portions are coupled to the central support elongated member; and
wherein the respective distal ends of the first and second curved portions are in contact with the inner surface of the tissue contacting member when the expandable-collapsible support structure is in the expanded configuration.

5. The intrauterine ablation device of claim 4, wherein the central bridge comprises a flexible ribbon or thin flexible membrane.

6. The intrauterine ablation device of claim 4, wherein the first curved portion and the second curved portion of the central bridge define respective concave surfaces that face each other when the expandable-collapsible support structure is in the expanded configuration.

7. The intrauterine ablation device of claim 6, wherein the first curved portion and the second curved portion of the central bridge further define respective convex surfaces in which the convex surface of the first curved portion faces the first inner flexure and the convex surface of the second curved portion faces the second inner flexure when the expandable-collapsible support structure is in the expanded configuration.

8. The intrauterine ablation device of claim 4, wherein an outer surface of the central bridge contacts the first inner flexure and the second inner flexure.

9. The intrauterine ablation device of claim 4, wherein the central bridge is configured to maintain the inner surface of the tissue contacting member in a spaced-apart configuration when the expandable-collapsible support structure is in the expanded configuration.

10. An intrauterine ablation device, comprising:
a central support elongate member configured for transcervical insertion;
an energy applicator operatively coupled to the central support elongate member, the energy applicator comprising a tissue contacting member and an expandable-collapsible support structure underlying the tissue contacting member, the expandable-collapsible support structure comprising outer flexures in lateral contact with an inner surface of the tissue contacting member and inner flexures disposed in between the outer flexures; and
a central bridge having a first curved portion and a second curved portion end, wherein the first and second curved portions ends of the central bridge are attached to respective middle portions of the inner flexures, wherein the central bridge is in contact with the inner surface of the tissue contacting member when the expandable-collapsible support structure is in an expanded configuration; and
wherein the respective proximal ends of the first and second curved portions are coupled to the central support elongate member.

11. The intrauterine ablation device of claim 10, wherein the central bridge comprises a flexible ribbon or thin flexible membrane.

12. The intrauterine ablation device of claim 10, wherein an outer surface of the central bridge contacts a first inner flexure and a second inner flexure.

13. The intrauterine ablation device of claim 10, wherein the central bridge is configured to maintain the inner surface of the tissue contacting member in a spaced-apart configuration when the expandable-collapsible support structure is in the expanded configuration.

14. The intrauterine ablation device of claim 10, wherein the first curved portion and the second curved portion of the central bridge define respective concave surfaces that face each other when the expandable-collapsible support structure is in the expanded configuration.

15. The intrauterine ablation device of claim 10, wherein the first curved portion and the second curved portion of the central bridge further define respective convex surfaces in which the convex surface of the first curved portion faces a first inner flexure and the convex surface of the second curved portion faces a second inner flexure when the expandable-collapsible support structure is in the expanded configuration.

16. The intrauterine ablation device of claim 1, wherein the first curved portion and the second curved portion of the central bridge define respective concave surfaces that face each other when the expandable-collapsible support structure is in the expanded configuration.

17. The intrauterine ablation device of claim 1, wherein the first curved portion and the second curved portion of the central bridge further define respective convex surfaces in which the convex surface of the first curved portion faces the first flexure and the convex surface of the second curved portion faces the second flexure when the expandable-collapsible support structure is in the expanded configuration.

18. The intrauterine ablation device of claim 1, wherein the central bridge is configured to maintain the tissue contacting member in a spaced-apart configuration when the expandable-collapsible support structure is in the expanded configuration.

\* \* \* \* \*